(12) United States Patent
Popovsky et al.

(10) Patent No.: US 7,987,547 B2
(45) Date of Patent: Aug. 2, 2011

(54) CLEANSING PAD

(75) Inventors: Michael Popovsky, Beverly Hills, CA (US); Yelena Popovsky, Beverly Hills, CA (US); Susanne Foote, Boise, ID (US); Shawna Lassen, Seattle, WA (US); Eric Jungermann, Phoenix, AZ (US); Maxwell Poper, Westminster, CA (US); Raulee Marcus, Hermosa Beach, CA (US)

(73) Assignee: Spongeables LLC, Inglewood, CA (US)

( * ) Notice: Subject to any disclaimer, the term of this patent is extended or adjusted under 35 U.S.C. 154(b) by 1263 days.

(21) Appl. No.: 10/562,311

(22) PCT Filed: Jul. 2, 2004

(86) PCT No.: PCT/US2004/021435
§ 371 (c)(1),
(2), (4) Date: Dec. 22, 2005

(87) PCT Pub. No.: WO2005/007789
PCT Pub. Date: Jan. 27, 2005

(65) Prior Publication Data
US 2006/0282966 A1    Dec. 21, 2006

Related U.S. Application Data

(63) Continuation-in-part of application No. 10/696,069, filed on Oct. 28, 2003, now abandoned.

(60) Provisional application No. 60/484,786, filed on Jul. 3, 2003.

(51) Int. Cl.
*A47L 13/17* (2006.01)
(52) U.S. Cl. .................. 15/104.93; 15/209.1
(58) Field of Classification Search ............... 15/104.93, 15/104.94, 209.1, 210.1
See application file for complete search history.

(56) References Cited

U.S. PATENT DOCUMENTS
389,296 A    9/1888    Greeley
(Continued)

FOREIGN PATENT DOCUMENTS
GB    907 867 A    10/1962
(Continued)

OTHER PUBLICATIONS
E.V. Bailey, "Industrial Oils," vol. 1, Chapter 8, p. 534.
(Continued)

*Primary Examiner* — Randall Chin
(74) *Attorney, Agent, or Firm* — Louis C. Paul, Esq.

(57) ABSTRACT

A cleansing pad (10) is made of a web of fibers, forming a substrate (11), where the substrate (11) includes a cleansing agent (12) therein. The cleansing agent (12) is a pourable soap. In making the cleansing pad (10), the cleansing agent (12) is initially heated from solid form into molten/liquid form, and distributed essentially throughout one or more portions of the substrate (11) in molten form to coat the fibers in said portions of the substrate (11). After application of the molten cleansing agent (12), the substrate (11) is then allowed to cool such that the molten cleansing agent (12) solidifies and remains solid at a desired range at and above room temperature, forming the cleansing pad (10). Thereafter, in use, the cleansing pad (10) is applied for cleaning an object in conjunction with a solvent such as water. The solvent dissolves the solidified cleansing agent (12). The cleansing pad (10) can be used in this manner multiple times without the need for application of additional cleansing agent (12) to the cleansing pad (10). As such, the cleansing pad (10) is a self-contained, long lasting product that maintains its creamy lather during multiple uses and does not require the user to reapply cleansing agents to the cleansing pad (10) with every use.

39 Claims, 18 Drawing Sheets

U.S. PATENT DOCUMENTS

| | | | |
|---|---|---|---|
| 2,320,858 A | 6/1943 | Field | |
| 2,820,768 A | 1/1958 | Fromont | |
| 3,094,735 A | 6/1963 | Hanlon | |
| 3,284,963 A | 11/1966 | Lanham et al. | |
| 3,810,841 A | 5/1974 | Richter | |
| 4,290,904 A | 9/1981 | Poper et al. | |
| 4,457,643 A | 7/1984 | Caniglia | |
| 4,515,703 A | 5/1985 | Haq | |
| 4,758,370 A | 7/1988 | Jungermann et al. | |
| 4,789,262 A | 12/1988 | Sanchez | |
| 5,022,517 A | 6/1991 | Benitez | |
| 5,152,809 A | 10/1992 | Mattesky | |
| 5,221,506 A | 6/1993 | Dulin | |
| 5,507,968 A | 4/1996 | Palaikis | |
| 5,955,417 A | 9/1999 | Taylor | |
| 5,960,506 A * | 10/1999 | Reuven | 15/104.93 |
| 5,994,281 A | 11/1999 | He et al. | |
| 6,171,007 B1 | 1/2001 | Hsu | |
| 6,187,728 B1 * | 2/2001 | McManus | 510/142 |
| 6,299,520 B1 | 10/2001 | Cheyne | |
| 6,386,778 B1 | 5/2002 | Guay et al. | |
| 2002/0173436 A1 | 11/2002 | Sonnenberg et al. | |

FOREIGN PATENT DOCUMENTS

| | | |
|---|---|---|
| GB | 1 180 995 A | 2/1970 |
| GB | 1 473 147 A | 5/1977 |
| GB | 2 084 176 A | 4/1982 |

OTHER PUBLICATIONS

Henry Goldschmeidt, "Transparent Soaps," Soap/Cosmetics/Chemical Specialties, Jun. 1972, pp. 37-38.

Dieter Osteroth, "Transparent Soaps," Soap/Cosmetics/Chemical Specialties, Oct. 1980, pp. 33-36, 74.

E. Jungermann and D. Taber, "Polyoxyethylene Alkylamides," Monionic Surfactants, Chapter 8, p. 207-246.

E. Jungermann and Henri C. Silberman, "Phosphorus-Containing Anionic Surfactants," Anionic Surfactants, Chapter 15, p. 495-578.

Mitchell S. Wortzman et al., "Soap and detergent bar rinsability," J. Soc. Cosmet Chem., Mar./Apr. 1986, p. 89-97, vol. 37.

European Patent Office, The Hague, Supplementary European Search Report for European Patent Application No. EP 04 77 7507 dated on Jun. 12, 2008, 3 pages.

* cited by examiner

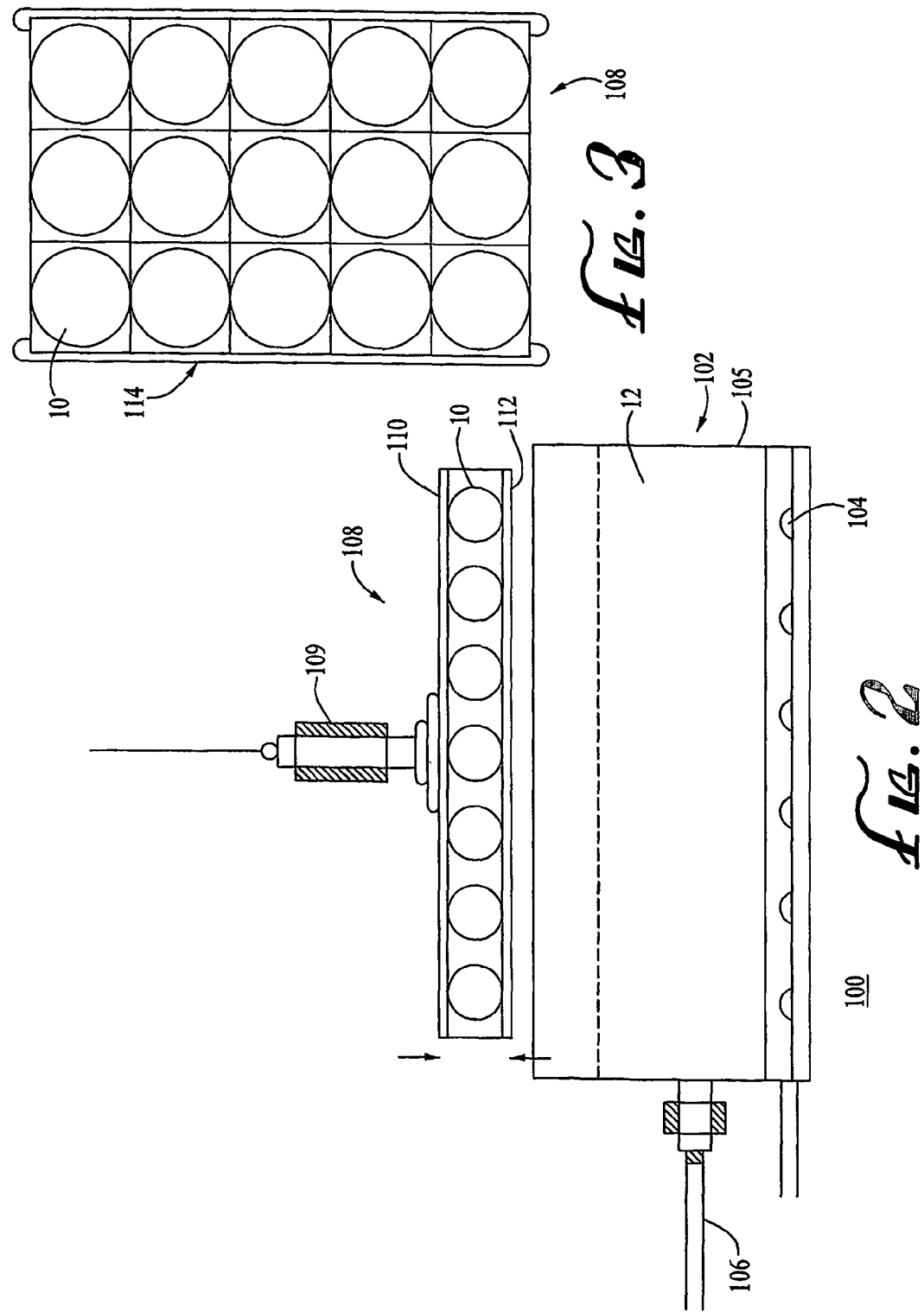

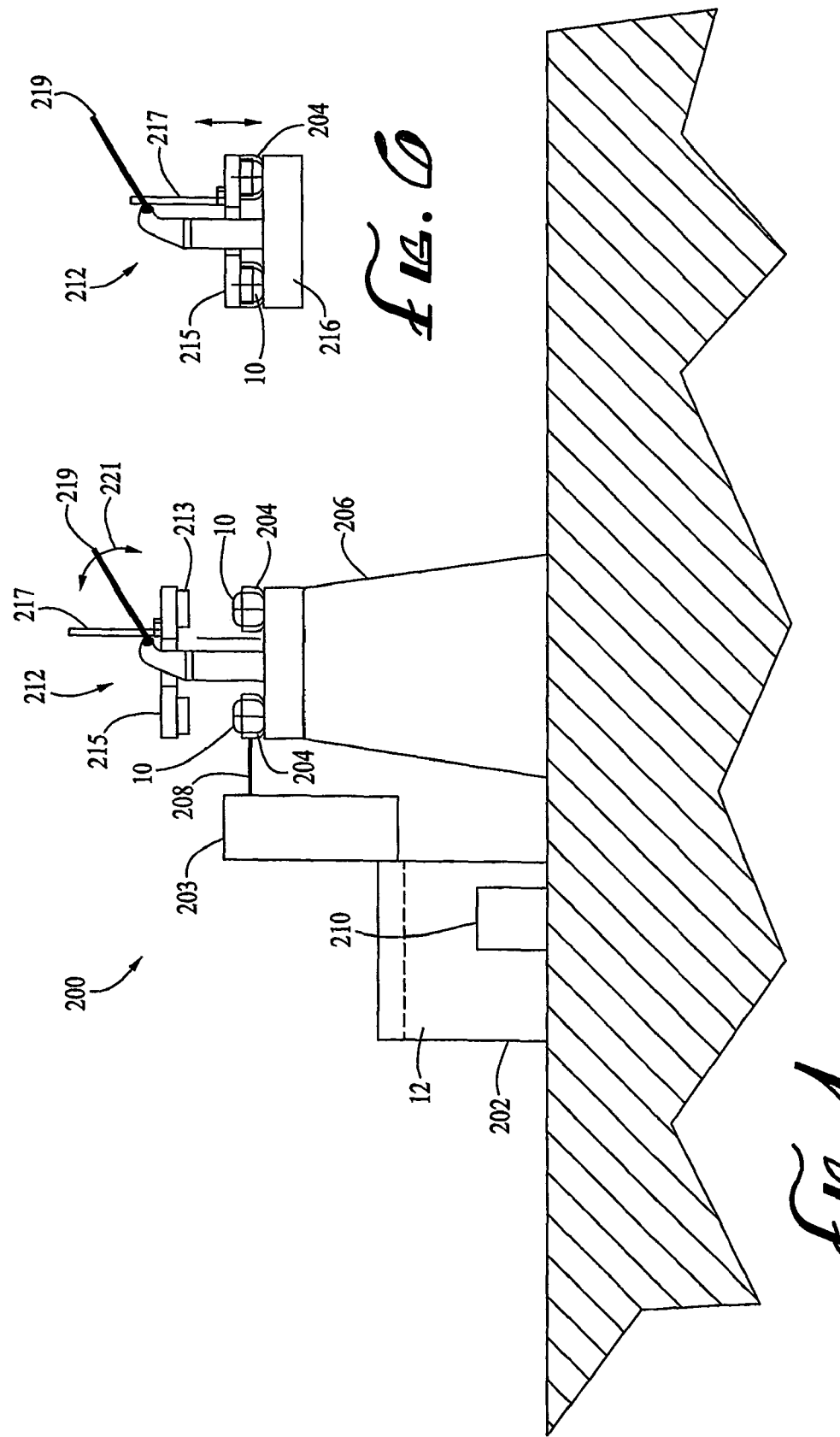

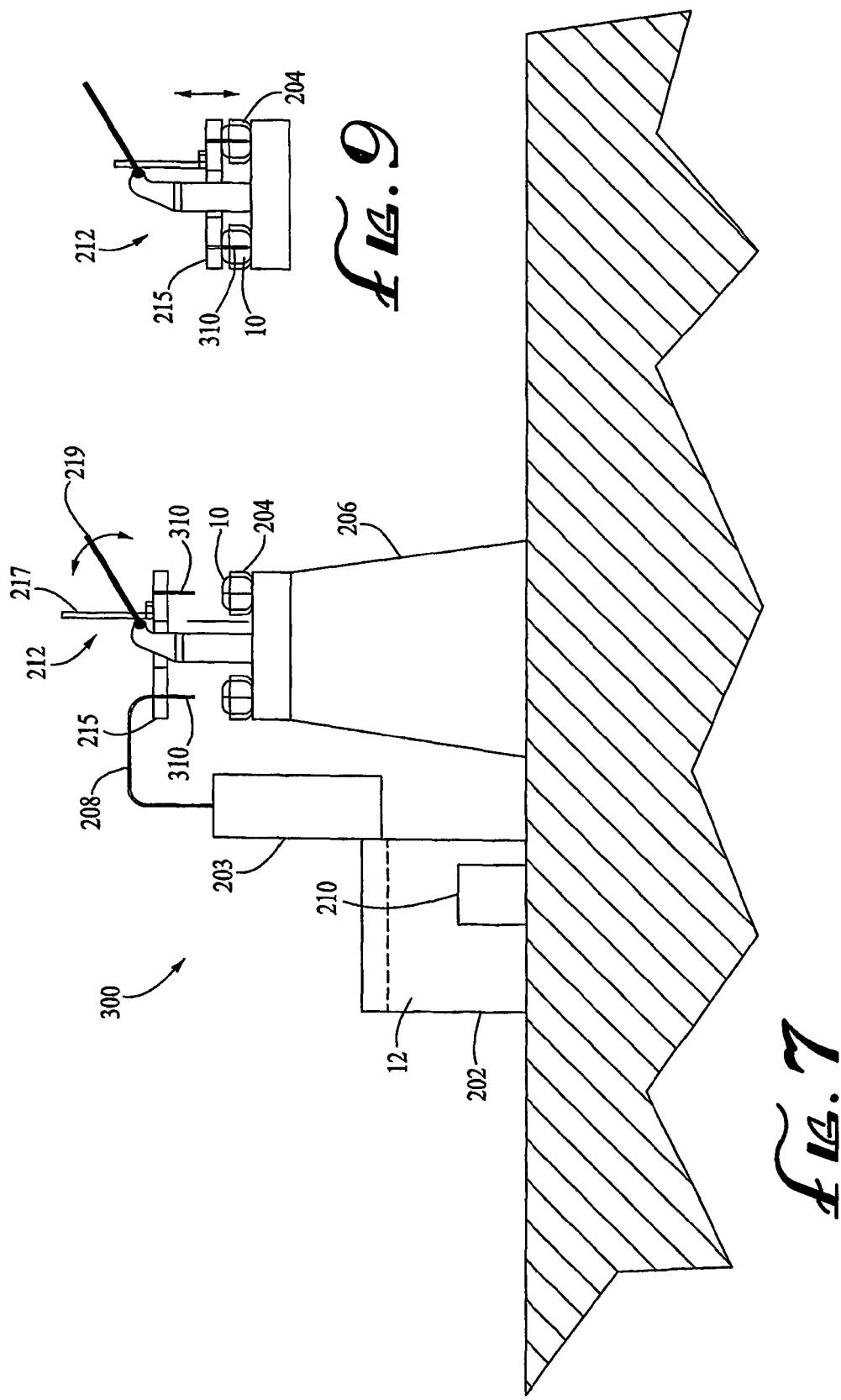

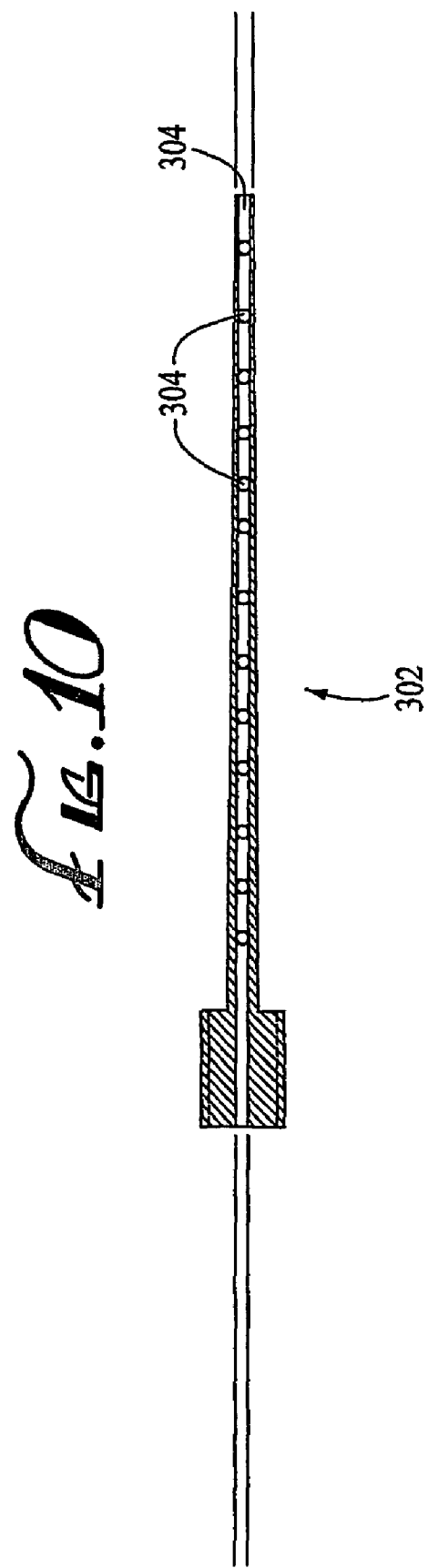

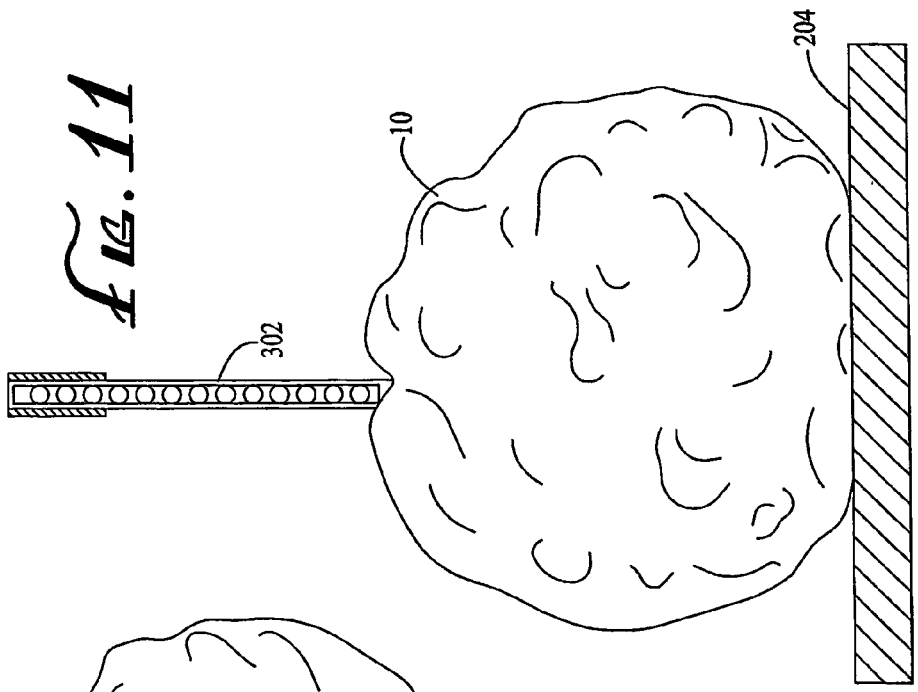
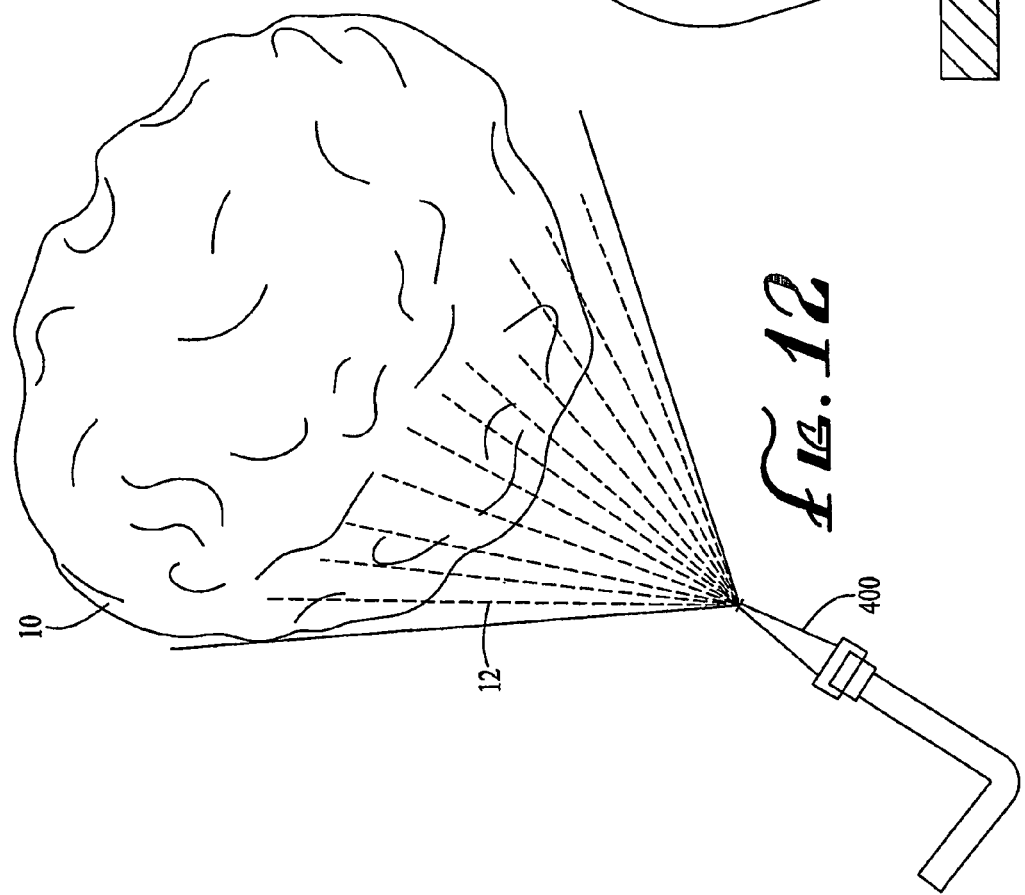

CLEANSING PAD

PRIORITY CLAIM

This is a continuation-in-part of U.S. application Ser. No. 10/696,069, entitled now abandoned, "Cleansing Pad", filed on 28 Oct. 2003, now abandoned incorporated herein by reference. Priority is claimed from the U.S. application Ser. No. 10/696,069, now abandoned and from U.S. Provisional Application No. 60/484,786, entitled "Soap and wash sponge", filed on 3 Jul. 2003, both of which are incorporated herein by reference.

TECHNICAL FIELD

The present invention relates to cleansing pads and processes for forming such cleansing pads with a cleansing composition therein.

BACKGROUND ART

Pads and natural and synthetic sponges have been used for cleaning purposes, such as cleansing the human body, removing dirt and dead skin, and moisturizing the cleansed skin. They have also been used to clean inanimate bodies/objects and the like. Typically, a user applies a cleansing compound to the pad or the surface to be cleaned, and then the pad is rubbed over the surface for cleaning action. The residual cleansing compound is then rinsed off the body or the surface.

A variation in the above process has been to create a cleansing pad by placing a cleaning agent such as bar of soap inside a sponge for washing the body in the shower or bath. Such a sponge includes a container forming an envelope/reservoir for the soap, and openings through to the container interior allowing water access to the soap and the facile exiting of lather for washing purposes. However, because the soap is in a reservoir, the lathering action may be limited because the lather must travel from within the reservoir through the sponge to the surface of the sponge for cleansing the body.

Other conventional cleansing pads provide metal meshes that are loaded up with soap paste and are used to clean metal and other surfaces, but not soft surfaces. Yet other conventional cleansing pads are aimed primarily at hard surface cleaning (kitchen/bathroom usage). In one case (U.S. Pat. No. 5,507,968) detergent is first blended with a polymeric material, such as polyacrylamide polymers, to become a controlled release detergent composition and this mixture is applied to a porous pad. However, a disadvantage in this case is the need for adding a polymer to the detergent.

In another case (U.S. Pat. No. 6,299,520) an antimicrobial substance is mixed into a liquid film forming binder, cured, and the combination is applied to various pads. In addition to antimicrobials, various abrasives can also be incorporated this way into the binder. However, a disadvantage in this case is the need for a liquid film forming binder for the antimicrobial agent.

Another case (U.S. Pat. No. 5,955,417) is directed to scouring pads wherein cleansing agents are injected into pads (0.8 to maximum 2.0 parts of dry cleanser to 1 part of pad) and the resulting product is force dried using a conventional two-stage convection drier to remove water. However, a shortcoming in this case is that the resulting product must be force dried to remove water. Another shortcoming in this case is that a maximum amount of 2 parts of dry cleanser to 1 part of pad is used which severely limits the number of usages.

There is, therefore, a need for a long lasting cleansing pad retaining sufficient amounts of cleansing agent, that allows multiple uses without the need for additional cleansing agents and does not require a multi-step drying process and does not require polymers for a cleansing agent to adhere to the pad.

DISCLOSURE OF THE INVENTION

The present invention addresses the above shortcomings and in one embodiment provides use of "pourable soaps" in cleansing pads resulting in several unexpected results, including long lasting, effectiveness of lather profile in hard water and providing a simpler process for incorporating a cleansing agent into a cleansing pad.

One of the objectives of the present invention is to provide a personal cleansing pad or cleansing sponge which cleans, lathers and rinses well in both soft and hard water, conditions, moisturizes the skin and which can last and maintain its lathering ability through multiple uses over an extended period of time.

Another objective of the present invention is to provide an improved, long lasting (multiple applications over a long period of time) cleansing system which cleans the skin with lather and which exfoliates and moisturizes the skin in a single washing and rinsing step.

It is a further objective of the present invention to provide a cleansing system which is milder to the skin with improved lather in both soft and hard water, which is longer lasting than the conventional cleansing systems and which rinses cleaner.

Another objective of the present invention is to provide a soap-based cleansing system including a cleansing agent comprising a pourable soap. Preferably, such a pourable soap is a soap formulation that is solid at temperatures up to about e.g. 120° F., but becomes a pourable liquid at higher temperatures, and resolidifies on cooling.

A further objective of the present invention is to provide a process and apparatus to add pourable soap in molten/liquid form to a pad (or other substrate) and that allows the soap to resolidify within the pad to form an integrated cleansing pad without the need for additional polymers or other additives.

Accordingly, in one embodiment the present invention provides a cleansing pad comprising a web of fibers, forming a pad, wherein the pad includes a cleansing agent therein. In one example of manufacturing such a pad, the cleansing agent comprises a pourable soap that is initially heated from solid form into liquid form, and distributed essentially throughout one or more portions of the pad in liquid form to substantially coat the fibers in said portions of the pad.

As such, in one version, essentially only the exterior of the pad is coated with the cleansing agent. In another version, the exterior of the pad is coated with the cleansing agent and portions of the interior of the pad are impregnated with the cleansing agent such that fibers of the pad are coated with the cleansing agent. In another example, essentially only portions of the interior of the pad are impregnated by the cleansing agent.

After application of the liquidified cleansing agent, the pad is then allowed to cool such that the cleansing agent solidifies and remains solid at a desired range above at and above room temperature, forming the cleansing pad. Thereafter, in use, the cleansing pad is applied for cleaning an object in conjunction with a solvent such as water. The solvent dissolves the solidified cleansing agent into a solution that includes quantities of the solvent and dissolved cleansing agent for cleansing the object. The cleansing pad can be used in this manner multiple times without the need for application of other cleansing agents to the cleansing pad. As such, the cleansing pad is a self-contained, long lasting product that does not require the user to reapply cleansing agents to the cleansing pad with every use.

The present invention further provides apparatuses for processes of impregnating the pads with cleansing agents such as by dipping, soaking, infusion, misting, spraying and the like, such that fibers of the pad are coated with the cleansing agent according to the present invention.

While the apparatuses and methods have or will be described for the sake of grammatical fluidity with functional explanations, it is to be expressly understood that the claims, unless expressly formulated under 35 U.S.C. 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 U.S.C. 112 are to be accorded full statutory equivalents under 35 U.S.C. 112. The invention can be better visualized by turning now to the following drawings wherein like elements are referenced by like numerals.

BRIEF DESCRIPTION OF THE DRAWINGS

FIG. 2 shows a side view of an embodiment of a dipping apparatus for a process of manufacturing a cleansing device pad according to the present invention;

FIG. 3. shows a bottom/top view of an example of the dipping basket in FIG. 3;

FIG. 4 shows a side view of an embodiment of another apparatus for a process of manufacturing a cleansing device pad according to the present invention;

FIG. 6 shows a side view of a press in the apparatus of FIG. 4;

FIG. 7 shows a side view of an embodiment of another apparatus for a process of manufacturing a cleansing device pad according to the present invention;

FIG. 9 shows a side view of a press in the apparatus of FIG. 7;

FIG. 10 shows a side view of an injector in the apparatus of FIG. 7;

FIG. 12 shows an example of spraying a pad with cleansing agent according to the present invention;

FIGS. 14 and 15 show different example perspective views of an embodiment of another apparatus for a process of manufacturing a cleansing device pad according to the present invention;

BEST MODES FOR CARRYING OUT THE INVENTION

Figure 1A:
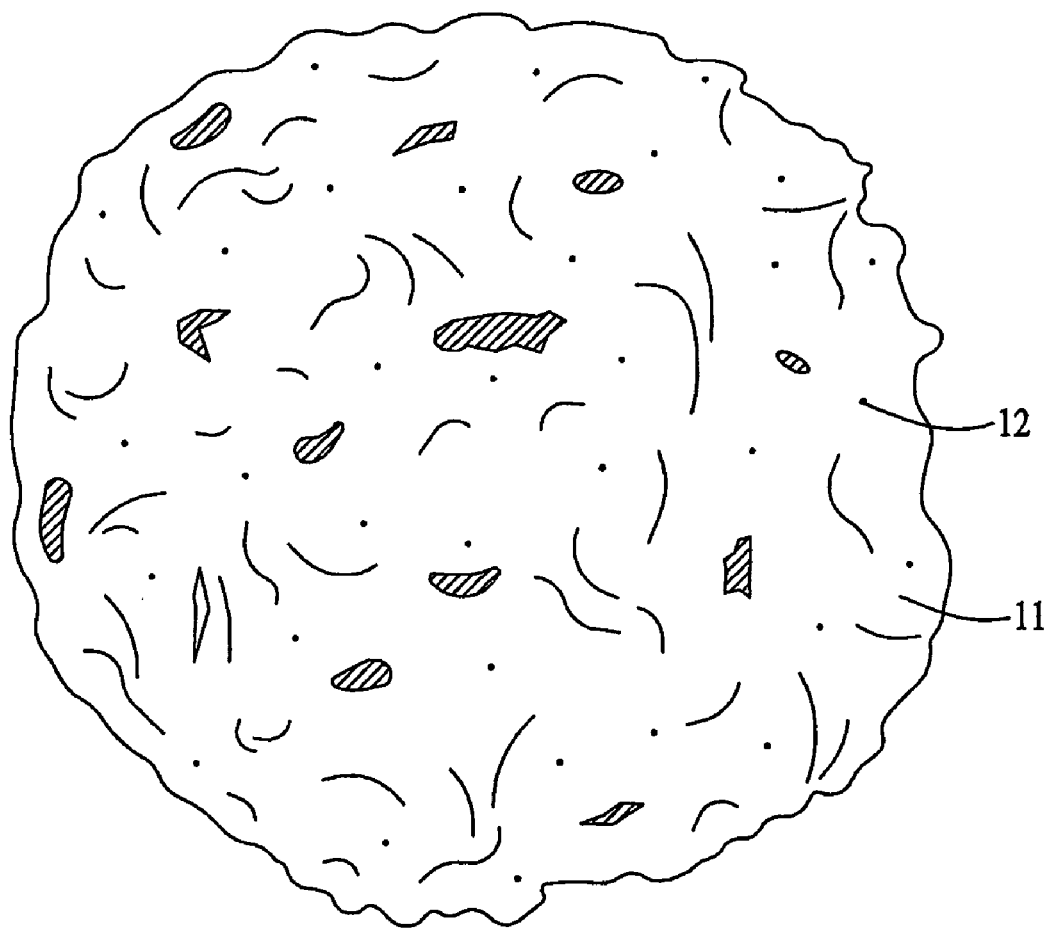
FIGS. 1A-B show example perspective and cross-section views, respectively, of a cleansing device pad according to an embodiment of the present invention.
Figure 1B:
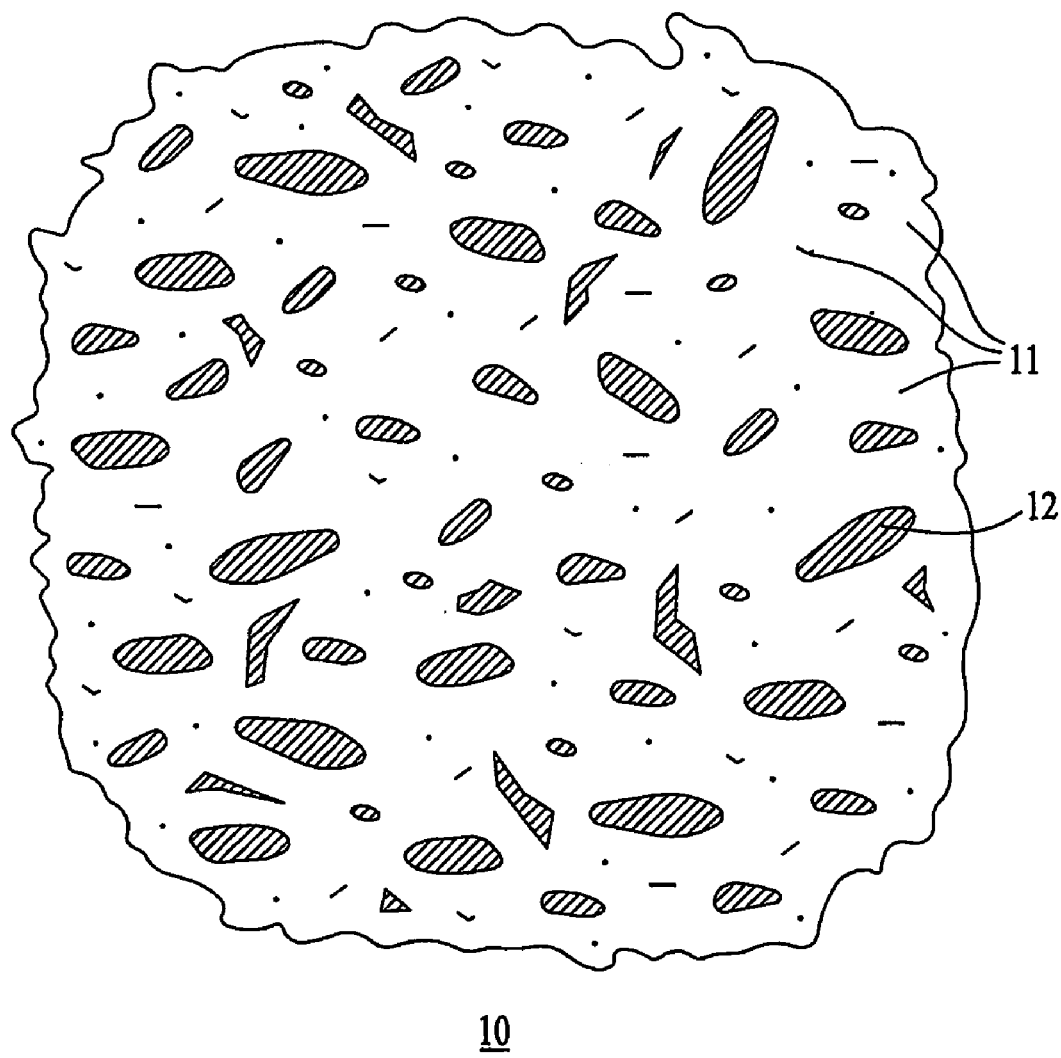

Referring to FIGS. 1A-B, in one embodiment the present invention provides a cleansing pad 10 comprising substrate made from a web of fibers forming a pad 11 and a cleansing agent 12 applied to the pad 11 to form the cleansing pad 10.

Although the term "pad" is utilized, the web of fibers form any functionally suitable shape and size. The pad 11 can be synthetic or naturally occurring, and can comprise e.g., porous materials, Polyurethanes (including but not limited to polyester, polyether, etc.), Cellulose, sponges, etc. Polyurethane is a general classification for all polymers that are formed from polyols and isocyanates. Polyester and Polyether polyurethanes refer to a subclass of these polymers. Polyethylene and polystyrene foams are made from ethylene and styrene monomers.

Other materials for the pad 11 may include all synthetic sponge materials, woven and non-woven materials, all natural including cotton and loofah-based. In addition, each pad 11 can be made of different materials on different sides and/or from center to surface of the pad 11. Further, the pad 11 can be anti-bacterially treated. Fragrances can be added to the cleansing agent 12 and colorants can be applied to the pad 11 as desired wherein, for example, different fragrances are matched with different colors. Further the pad 11 can be multi-colored. Preferably, the color remains stable in the manufacturing processes described herein, such as example within operating temperature range of e.g. about 120 to 200° F.

Other ingredients that can be added to the cleansing agent 12 include e.g. anti-cellulite, anti-aging substances, herbal substances, natural and synthetic extracts (e.g., hyaluronic acid, etc.), and so on. Further, active ingredients such as sunscreen agents, antimicrobials, antiseptics, healing agents, etc. can be added to the cleansing agent 12.

Pad compressibility, density and porosity affect absorption of the cleansing agent 12 into the pad 11. Compressibility (resistance) of the pad 11 is selected based on upper and lower control limits for desired results. Example resistance for the pad 11 can be in the e.g. 2.5 to 3.5 kilo Pascal (1.5 to 3 psi) range. Pad density is also selected based on desired results and can be in the e.g. 31 to 33 kilos per meter cubed range. Porosity is a function of size and appearance of pore structure of the pad 11. Reticulated pads (open pore) or unreticulated pads (pore not open) can be used, however non-reticulated pads are better at holding the cleansing agent 12. In either case, example pore size can be 3 to 100 pours per inch.

In one example, a pad 11 can comprise a sponge that is about 4½ inches in length/width that is dipped/submerged into one or more colored, plain opaque or clear molten cleansing agent 12, wherein the cleansing agent 12 cools to a solid form on the exterior and/or interior of the sponge 11 to form the cleansing pad 12. The sponge 11 and the cleansing agent 12 can be selected such that the cleansing pad 10 is suitable for various applications such as human bathing or washing objects of any sort such as dishes, appliances, surfaces, vehicles, etc. The cleansing pads 10 can also be scented with fragrances, essential oils, etc. as desired.

Although in the following description the terms "pad" and "sponge" are used interchangeably for simplicity of description, it is to be understood that that a sponge is only one example of a pad 11. Similarly, although the terms "cleansing pad" and "cleansing sponge" are used interchangeably for simplicity of description, it is to be understood that a sponge is only one example of a pad 11.

The cleansing agent 12 comprises a soap that is solid at certain temperatures, but becomes a pourable liquid at higher temperatures (i.e., "pourable soap"). Upon cooling, the soap resolidifies. A requirement is a relatively low melting point of pourable soaps and the ability to resolidify on cooling. Typical transparent soaps that have such pourable properties, also known as glycerine soaps, are usually manufactured by the "semiboiled" or the "cold" process, whereby a mixture of fats is reacted with a solution of strong alkali in an amount very nearly equal to that needed for complete saponification (See e.g., E. Jungermann, "Bailey's Industrial Oil and Fat Products", Vol. 1, Chapter 8, pg 534 John Wiley & Sons, New York, N.Y. (1979), incorporated herein by reference). The glycerine liberated by the saponification reaction is allowed to stay in the resultant soap mass. Certain additives are added to the transparent soap mass which tend to provide a gel state to the soap mass and depress the development of fibrous crystals. Such additives frequently used include additional glycerine, sugars, such as sorbitol, ethyl alcohol, aminoalcohols and various polyols. The fats and oils used in the production of pourable soaps can include, but are not limited to, coconut, palm, palm kernel, castor oil and tallow. Other oils that can be used to modify the characteristics of the finished soap may include hemp, jojoba, olive, safflower, soya oil and similar materials. Some typical example pourable soap formulations are shown in Table A below:

TABLE A

Some Typical Pourable Soap Formulas (pan charges)

| Palm oil | 50 | 80 | 75 | 58 | 75 |
|---|---|---|---|---|---|
| Coconut oil | 30 | 100 | 75 | 17 | 20 |
| Castor oil | 10 | 80 | 0 | 8 | 0 |
| Rosin | 5 | 0 | 50 | 17 | 5 |
| Caustic Soda, 37 Be | 51 | 133 | 100 | 47 | 51 |
| Ethyl Alcohol | 60 | 30 | 80 | 25 | 60 |
| Sugar (50% solution) | 0 | 180 | 80 | 0 | 0 |
| Glycerine added | 5 | 0 | 0 | 25 | 5 |
| Perfume, color | | | QS | | |

Reference: H. Goldschmidt, Soap, Cosmetics, Chemical Specialties, 48, 37-38 (June 1972), incorporated herein by reference.

The formulations above are produced by saponifying the fats in the presence of alcohol in a closed reactor with a condenser to control alcohol loss. The fat charge is heated to about 60° C. and alkali is added slowly. After saponification is completed, the additional glycerine, sugar solution, etc. are added. Free alkali is adjusted, additives such as perfumes and color can be added, and the solution poured into frames and allowed to cool. Because of the use of alcohol and rosin in the older transparent soaps, these soaps had a tendency to cause skin dryness. One approach to overcoming this problem was the elimination of the use of ethyl alcohol including a formulation based on mixed sodium and triethanolamine soaps superfatted with a fatty acid (See e.g. U.S. Pat. No. 2,820,768, incorporated herein by reference). Such a soap was reported to be mild and to have superior rinseability (See Wortzman, M. S., R. A. Scott, P. S. Wong, N. J. Lowe and J. Breeding, J. Soc. Cosm. Chem. 37, 89-97 (1986), incorporated herein by reference). These formulations behaved like "pourable soaps".

An example method of manufacturing a cleansing pad 10 according to the present invention includes heating the pourable soap 12 above its melting point and pouring it into a heated metal bath. Additives such as fragrances, coloring, moisturizers, antimicrobials, etc. may be added at this stage. The molten soap 12 is applied to a pad 11 comprising e.g. a sponge, until the sponge 11 absorbs the molten soap 12 and then allowed to cool to e.g. room temperature for the molten soap 12 to resolidify, forming a cleansing sponge 10.

Suitable pourable soaps 12 can be melted and resolidified without change in composition, without forced cooling to solidify it, and without volatilizing e.g. fragrance and other ingredients that might be destroyed in high temperatures. In one example, such pourable soaps can be heated to about 40° F. above their melting point wherein the molten soap is not held at this elevated temperature for more than e.g. 6 hours. If additives (e.g., fragrances) to the pourable soaps are negatively affected by such a treatment, then temperature, mixing time, and holding time can be controlled to reduce such negative effects.

Other suitable pourable soaps 12 are chemically stable above their melting temperatures and can be held at such temperatures for up to e.g. 12 hours and resolidify as they cool below that temperature. Examples of pourable soaps 12 include soaps that are solid at room temperature and melt in a temperature range of about 120° to 160° F.

An example of pourable soap 12 that can be used in the preparation of the cleansing pad 10 herein includes soaps comprising: (a) about 25 to 55% sodium or potassium soaps or combinations thereof derived from a combination of oils, such as coconut, palm, palm kernel, tallow, castor and/or safflower oil, (b) about 5 to 30% added glycerine, (c) about 0 to 10% sorbitol, and (d) minor additives and water. The pourable soap is melted, and the molten soap is applied to the sponge 11 to result in the impregnated cleansing sponge 10 with a soap:sponge weight ratio ranging between 2:1 to 10:1. Preferred range is about 7 or 8:1. Another example utilizes the formulation above, but includes about 1 to 15% of a fatty acid, such as stearic, palmitic, oleic, isostearic, linoleic, or coco fatty acid, etc., in order to neutralize excess alkali and to act as a superfatting agent to provide improved skin feel and foam stability.

In another variation on the above approach, the saponification reaction is carried out in the presence of an amino alcohol, such as e.g. triethanolamine, to yield a combination of sodium soaps and triethanolamine (TEA) soaps. In this case, the excess stearic acid reacts with the triethanolamine to neutralize excess caustic soda and o form triethanolamine stearate soap. The amounts of the amino alcohol used in this reaction range from about 5% to 30%.

In yet another variation, certain surface active agents can be added to the above formulations to act as foam boosters, foam stability enhancers, and as lime soap dispersants (See e.g., Anionic Surfactants, Part I & II, W. M. Linfield editor, Marcel Dekker, Inc., N.Y. (1976), incorporated herein by reference; and Nonionic Surfactants, Martin J. Schick, editor, Marcel Dekker, Inc. N.Y. (1966), incorporated herein by reference). Examples of surface active agents include anionic, nonionic and amphoteric surfactants and combinations thereof at levels ranging from about 1% to 15% on an active basis. Preferred levels can be about 2 to 10% on an active basis. Some typical examples include: sodium and/or ammonium or TEA lauryl sulfate, sodium and/or ammonium laureth sulfate, cocodiethanolamide, lauryl monoethanolamide, cocoamidopropyl betaine, ethoxylated lauryl alcohols (degree of ethoxylation n=1 to 50), sodium methyl cocoyl isethionate, sodium methyl cocoyl taurate, lauryl dimethyl amine oxide, sodium lauroyl sarcosinate, alpha-sulfostearic acid and esters, alkyl glyceryl ethers and esters, etc.

In the following example, pourable soap formulations (Examples of prepared formulations #1 to #9 are shown in Table 1 below) according to the present invention are expressed as weight percentages of the pourable soap 12. The pourable soaps 12 in this group represent sodium and triethanolamine (TEA)-based superfatted soaps from triglyceride oils superfatted with excess fatty acids, such as stearic. In these examples, the pourable soaps 12 are prepared as follows: coconut and palm oil are added to triethanolamine, heated to about 50° C., followed by slow addition of a about 33% caustic soda solution and allowing temperature to rise to about 80° C. The amount of caustic soda (NaOH) used is about 5% excess needed to saponify the coconut and palm oils. After saponification is complete, the excess is neutralized with stearic acid. The remainder of the stearic acid (as TEA stearate) acts as a superfatting agent. Glycerine is added and stirred at about 80° C. continuously for about 15 minutes. The solution is then allowed to solidify. Thereafter, the soap 12 is melted, and the molten soap 12 applied to the sponge 11.

TABLE 1

| Ingredients | Examples | | | | | | | | |
|---|---|---|---|---|---|---|---|---|---|
| | #1 | #2 | #3 | #4 | #5 | #6 | #7 | #8 | #9 |
| Triethanolamine (99%) | 28.0% | 28.0% | 28.0% | 28.8% | 28.8% | 28.8% | 28.5% | 28.5% | 28.5% |
| Coconut Oil | 14.1% | 17.1% | 18.5% | 7.8% | 8.8% | 8.2% | 8.2% | 9.0% | 10.0% |
| Palm Oil | 14.1% | 17.1% | 19.6% | 31.4% | 35.2% | 33.3% | 33.3% | 36.0% | 40.0% |
| Glycerine | 8.0% | 8.0% | 8.0% | 8.0% | 8.0% | 8.0% | 8.0% | 8.0% | 8.0% |
| Stearic | 21.0% | 15.0% | 10.0% | 10.0% | 10.0% | 10.0% | 5.0% | 5.0% | 5.0% |
| NaOH[1] | | | | | QS | | | | |

[1] 5% excess to saponify coconut and palm oil

Foam tests for the above soap formulations were carried out as follows: about ml of 5% soap solution and 1 ml olive oil were added to about 200 ml distilled water in a stoppered 500 ml cylinder and the volume was brought up to 250 ml with additional distilled water. This represented a soap concentration of 1 g/liter. The lather results are shown below in relation to the example formulations #1 through #8 in Table 1 above:

| | Examples | | | | | | | | |
|---|---|---|---|---|---|---|---|---|---|
| | #1 | #2 | #3 | #4 | #5 | #6 | #7 | #8 | #9 |
| Soft Water Foam Volume, ml | 80 | 125 | 155 | 170 | 185 | 185 | 155 | 130 | 130 |

Foam volume is that reached after gently inverting the cylinder 10 times in 25 seconds, less 250 ml. Desirable results from a foaming point of view in this series were obtained using about 10% stearic acid for superfatting, a fat charge of about 41.5 to 44.0% and a palm:coconut oil ratio of 80:20.

Example formulation 10 below (Table 2) refers to pourable soaps 12 that contain a relatively high level of glycerine and other agents such as sorbitol to assure the formation of a pourable soap. The pourable soaps 12 in this group represent soaps based on triglyceride oils (percentages in Table 2 are by weight basis):

TABLE 2

Example #10

| Ingredients | ranges | preferred |
|---|---|---|
| Glycerine | 10-30% | 20% |
| Sodium Cocoate | 8-20% | 19% |
| Sodium Palmitate | 12-20% | 16% |
| Sodium Ricinolate | 9-17% | 15% |
| Safflower Oil Soap | 2-5% | 4% |
| Sorbitol | 0-8% | 4% |
| Sorbitan Oleate | 2-8% | 4% |
| Soybean Protein | 2-8% | 2% |
| Titanium Dioxide | 0-0.2% | 0 |
| Purified Water | | QS |

Example formulation 11 below (Table 3) refers to pourable soaps 12 which combine sodium soaps similar to the example formulation 10 above, with synthetic detergents in order to increase the hard water compatibility and foaming characteristics of the soaps. The pourable soaps 12 in this group represent soaps based on triglyceride oils combined with synthetic surfactants (e.g., sodium soaps containing about 5 to 35% glycerine and/or 0-10% propylene glycols or similar low molecular weight polyhydroxy compounds) to which synthetic detergents such as sodium lauryl sulfate, cocoamido propyl betaine, and/or sodium laureth sulfate have been added in the range of about 1-7% each on an active basis.

TABLE 3

Example #11

| Ingredients | ranges | preferred |
|---|---|---|
| Glycerine | 14-25% | 16.0% |
| Sodium Cocoate | 8-16% | 12.0% |
| Sodium Palmitate | 11-20% | 16.0% |
| Propylene Glycol | 0-6% | 3.0% |
| Sorbitol | 0-8% | 5.0% |
| TEA Lauryl Sulfate (40% a.i.) | 5-12% | 7.5% |
| Cocoamidopropyl Betaine (28% a.i.) | 5-10% | 7.5% |
| Sodium Laureth Sulfate (30% a.i.) | 5-15% | 10.0% |
| Sodium Oleate | 1-3% | 1.2% |
| Acetamide MEA | 0-5% | 3.0% |
| Purified Water | | QS |

Other example pourable soaps 12 below (Example formulations #12 to #32 in Tables 4 and 5) are based on formulation #5 in Table 1 above, to which a variety of additives are added. Any of the soap bases in Example formulations #1 to #11 above can also be used in combination with these additives. Example additives include: antimicrobial agents, fragrances, moisturizers, abrasives, skin conditioners, chelating agents, antioxidants, preservatives, colors, etc. The additives are added to the molten soap 12 with appropriate stirring action prior to application to the sponge 11 to form the cleansing sponge 10.

TABLE 4

| Ingredients | #12 | #13 | #14 | #15 | #16 | #17 | #18 | #19 | #20 | #21 | #22 |
|---|---|---|---|---|---|---|---|---|---|---|---|
| Formulation #5 | 99.0% | 99.0% | 99.5% | 97.0% | 99.5% | 95.2% | 98.7% | 98.0% | 95.0% | 80.0% | 94.0% |
| Fragrance | 1% | 0% | 0% | 0% | 0% | 0% | 0% | 0% | 0% | 0% | 0% |
| Wasabi Extract | 0% | 1% | 0.05% | 0% | 0% | 0% | 0% | 0% | 0% | 0% | 0% |
| Acetamide MEA | 0% | 0% | 0% | 3% | 0% | 0% | 0% | 0% | 0% | 0% | 0% |
| Triclosan | 0% | 0% | 0% | 0% | 0.5% | 0% | 0% | 0% | 0% | 0% | 0.4% |
| PEG-6 Methyl Ether | 0% | 0% | 0% | 0% | 0% | 4% | 0% | 0% | 0% | 0% | 4.6% |
| Triclocarbam | 0% | 0% | 0% | 0% | 0% | 0.8% | 0% | 0% | 0% | 0% | 1% |
| Lanolin Alcohol | 0% | 0% | 0% | 0% | 0% | 0% | 1.3% | 0% | 0% | 0% | 0% |
| Sucrose Cocoate (ESAC80) | 0% | 0% | 0% | 0% | 0% | 0% | 0% | 2% | 5% | 0% | 0% |
| TEA Lauryl Sulfate (40%) | 0% | 0% | 0% | 0% | 0% | 0% | 0% | 0% | 0% | 20% | 0% |

TABLE 5

| Ingredients | #23 | #24 | #25 | #26 | #27 | #28 | #29 | #30 | #31 | #32 |
|---|---|---|---|---|---|---|---|---|---|---|
| Formulation #5 | 95% | 85% | 75% | 98% | 80% | 99% | 97% | 90% | 95% | 98% |
| Aloe Vera 2% Gel | 5% | 15% | 0% | 0% | 0% | 0% | 0% | 0% | 0% | 0% |
| Sodium Cocoly Sulfate (28%) | 0% | 0% | 25% | 0% | 0% | 0% | 0% | 0% | 0% | 0% |
| Isopropyl Palmitate | 0% | 0% | 0% | 2% | 0% | 0% | 0% | 0% | 0% | 0% |
| Sodium Sarcosinate (30%) | 0% | 0% | 0% | 0% | 20% | 0% | 0% | 0% | 0% | 0% |
| Hyaluronic Acid | 0% | 0% | 0% | 0% | 0% | 1% | 0% | 0% | 0% | 0% |
| Alkylpolysaccharide | 0% | 0% | 0% | 0% | 0% | 0% | 3% | 0% | 0% | 0% |
| Sodium Cocoyl Isethionate | 0% | 0% | 0% | 0% | 0% | 0% | 0% | 10% | 0% | 0% |
| Cyclic Polydimethylsiloxane | 0% | 0% | 0% | 0% | 0% | 0% | 0% | 0% | 5% | 0% |
| Safflower Oil | 0% | 0% | 0% | 0% | 0% | 0% | 0% | 0% | 0% | 2% |

Further, the pourable soap 12 can comprise sodium soaps in addition to materials such as sugars, ethyl alcohol, rosins, polyhydroxy compounds, such as glycerine or propylene glycols which contribute to the "pourability properties" of these soaps. The pourable soap 12 can also include synthetic having a combination of: (a) anionic synthetic detergents, such as e.g. sodium and/or ammonium lauryl sulfate, TEA lauryl sulfate, sodium or ammonium laureth sulfate, sodium cocoyl isthionate and related materials, etc., (b) amphoteric detergents, such as e.g. cocoamidopropyl betaine or cocodimethyl amine oxide, etc. and (c) Nonionic detergents such as e.g. ethoxylated long chain alkyl alcohols or esters such as sorbitan oleate, etc.

Preferably, the preheat/melting temperature for the solid soap 12 is selected to be the lowest possible consistent with the selected manufacturing process. The preheating can begin about 1 to 2 hours before application to the sponge 11 to form the cleanings sponge 10, so as not to accelerate oxidation/discoloring of the molten soap 12. This can be perform in a small electric kettle/vessel of size sufficient to support production use rates. The kettle can be both time and temperature controlled and may include an agitation system to prevent "wall scalding" of the molten soap 12.

Based on a number of the above formulations, lathering was determined on the soaps alone, and the cleansing sponge 10 (i.e., the soap-sponge combination). In the former case, the lathering was evaluated in soft (distilled) water to determine the relative performance of soap-based formulations, which normally do not foam well in hard water (>150 ppm). The cleansing sponges 10 were evaluated in hard water which produced the unexpected result of a synergistic foaming effect even in hard water.

The cleansing sponge 10 according to embodiments of the present invention also unexpectedly increases the life of the soap 12 in two ways: (1) the sponge 11 adds more air into the lather which requires a smaller amount of soap 12 to cleanse (making the soap 12 last longer than when used alone) and (2) the sponge 11 acts as a shelter to protect the soap 12 from evaporating. The sponge 11 helps control the amount of soap 12 used in the cleansing sponge 10. The combination of the sponge structure and soap provides the foamability of the soap 12 even in very hard water (>300 ppm).

For different size sponges 11 different amounts of soap may be utilized. Further, different amounts of soap 12 in one sponge 11 can last for different number of uses. For example, 6 oz for up to 30 showers; 4 oz for up to 21 showers, and 1 oz for up to 10 showers. There can be a varying soap to sponge ratio based on soap formulation, and composition/size of the sponge 11, and the amount of soap 12 can be correlated to use rate of the cleansing sponge 10. As such, the factors that can be used in determining ratio of soap 12 to sponge 11 include formulation of the soap 12, weight of the sponge 11, compression of the sponge 11, composition of the sponge 11, type of manufacturing process (e.g., multiple immersions, spraying, combination, etc.) and desired number of reuses of the resulting cleansing sponge 10. Embodiments of the present invention provide a broad range of soap to sponge weight ratio from about 1 to 1 to about 10 to 1. This provides a high rate of reusability for the cleansing sponge 10.

In use of the cleansing sponge 10, application of hard or soft water and applied pressure creates lather from the soap 12 that was impregnated or coated in the sponge 11. For example, the user places the cleansing sponge 10 under or in water, and applies pressure with hand whereby a foamy lather will ensue from the water dissolving the soap 12. Then the cleansing sponge 10 can be applied directly to human body or other objects for washing. After washing, the user slightly squeezes the cleansing sponge 10 to wick away excess water and sets it aside, or hangs with a loop and or loop-clamp attached to sponge, for the cleansing sponge 10 to dry. In one example version, the loop-clamp comprises a plastic loop approximately 2 inches in length ending in a metal flat nosed clamp. The user squeezes the clamps with fingertips and attaches to the cleansing sponge 10 (e.g., sponge ball or dye cut).

The cleansing sponge 10 can be used in this manner multiple times without the need for application of other soap to the cleansing sponge 10. As such, the cleansing sponge 10 is a long lasting product that does not require the user to reapply soap to the sponge 11 with every use. In one example, with 6 oz soap impregnated in the cleansing sponge 10, the cleansing sponge 10 can be used for thirty showers once a day for about 10 to 15 rubs per shower. In another example, with 7 oz of soap impregnated in the cleansing sponge 10, the cleansing sponge 10 can be applied for thirty days, one shower a day, wherein approximately 0.2 to 0.3 oz of soap in the cleansing sponge 10 are used per application.

Different processes and corresponding apparatuses/equipment for manufacturing cleansing pads (e.g., cleansing sponges) 10 according to an embodiment of the present invention are described below. As those skilled in the art will recognize, other processes and corresponding equipment can also be used in manufacturing cleansing pads 10 according to the present invention. Examples of applying the soap 12 to the sponge 11 according to the present invention such that fibers of the sponge 11 are coated with the soap 12 include dipping/soaking, spraying, injection/infusion, misting, etc., described further below.

Referring to FIG. 2, an embodiment of an apparatus 100 for manufacturing a cleansing sponge 10 according to an embodiment of the present invention is shown. The cleansing agent (e.g., "pourable soap") 12 that is in solid form at, e.g., room temperature, is heated to about 120 to 200° F. and maintained in molten (i.e., liquid) form in a soap vessel/kettle 102 by electric or gas burning heating elements 104.

Alternatively, the soap 12 can be heated into molten form elsewhere and transferred to the vessel 102 via a pipe 106. The molten soap temperature should be low consistent with the dipping process such that the molten soap 12 can flow depending on pipe width. One or more sponges 11 are placed in a slotted basket 108 suspended by a support 109, wherein the basket 108 is lowered into the molten soap 12, such that the sponges 11 are submerged in the molten soap 12 and allowed to absorb the molten soap 12.

The duration of submerging the sponges 11 (i.e., immersion time) can be varied to control the amount of molten soap 12 absorbed by the sponges 11. Immersion time can be about e.g. 5 to 50 seconds and preferably less than 10 seconds. The immersion time may depend on particular soap formulations. Some formulations may require longer or shorter immersion affected by sponge materials and densities. For example, a short duration for submerging (immersing) the sponges 11 in the molten soap 12 essentially coats only the exterior of the sponges 11 with the molten soap 12. Longer periods of submersing the sponges 11 allows coating of the interior fibers of the sponges 11 as well. Other factors that can be varied to control the amount of coating of the fibers in the sponges 11 include varying viscosity of the molten soap 12, the porous nature of the sponges 11, the material of the sponges 11, etc. (described further below). For example, larger pores of a sponge 11 soak up more molten soap 12, whereas smaller/tighter pores of a sponge 11 allow for less molten soap 12 to be soaked up if the material of the sponges is held constant. On the other hand, different materials absorb and retain pourable soap at different rates, given that the pore size is held constant.

Preferably, the sponges 11 are compressed as immersed into the molten soap 12 to allow better soap absorption. The compression range of the sponges 11 can be e.g. 0.5 to 5.0 inches, wherein the compression range is the level to which each sponge 11 is compressed after immersion in the molten soap 12. The compression range can be adjusted based on the differences in sponge materials and densities. In the example of FIG. 2, the sponges 11 can be compressed between upper and lower squeezing plates 110, 112 in the basket 108, and the pressure is slowly released for the sponges 11 to absorb the molten soap 12 while submerged/immersed therein, to coat the fibers inside each sponge 11. When the pressure is released, each sponge 11 holds the absorbed molten soap 12 therein. In either case, the amount of molten soap 12 is premeasured into the vessel 102 where the sponges 11 are submerged.

As shown by example bottom view in FIG. 3, the basket 108 can be a flat bottomed, open slotted basket which holds several sponges 11. The sides 114 of the basket 108 are equal in height and length to the walls 105 of the soap holding/warming vessel 102. The basket 108 along with the sponges 10 are immersed in the molten soap 12 in the vessel 102, wherein the sponges 11 will remain floating, but in an even fashion, as the surrounding area around each sponge 11 allows little movement. Application of selected amount of pressure to the sponges 11 via the plates 110, 112, allows measured absorption of the molten soap 12 by the sponges 11 when the pressure is released.

Immersion depth of the sponges 11 can be 1 to 40 inches, wherein the immersion depth is depth to which the sponges 11 are immersed into the molten soap 12 in the dipping vessel (tank) 102. The immersion depth can be adjusted based on materials of the sponges 11. Some sponges 11 may require deeper or shallower immersion. Immersion depth may also affect sponge absorption due to uneven heat distribution around the sponges 11.

After dipping, the basket 108 is raised via the support 109 to take the soaked sponges 11 out of the molten soap 12. When the basket 108 is raised out of the vessel 102, excess molten soap 12 drips off the sponges 11. In one example, each sponge 11 retains e.g. about 1 to 8 oz. of molten soap 12. This amount can be selected by controlling/measuring the temperature/viscosity of the molten soap 12. In another version, after the sponges 11 are taken out of the soap 12, preferably the sponges 11 are squeezed to extract out excess soap. The speed with which the sponges 11 are squeezed can be e.g. 1 to 6 times per second, wherein the selected speed is also a function of sponge material and density. The basket 108 is then transferred to a drying/cooling area for a specified duration of time for the molten soap 12 to resolidify in the sponges 11 based on the selected characteristics of the soap 12, forming the cleansing sponge 10. In one example, the cooling/drying step is not a forced step for removing excess water, wherein the processed sponges 10 are allowed to cool by exposure to ambient temperature such as room temperature. Alternatively, an induced artificial cooling step may be utilized.

Figure 5:
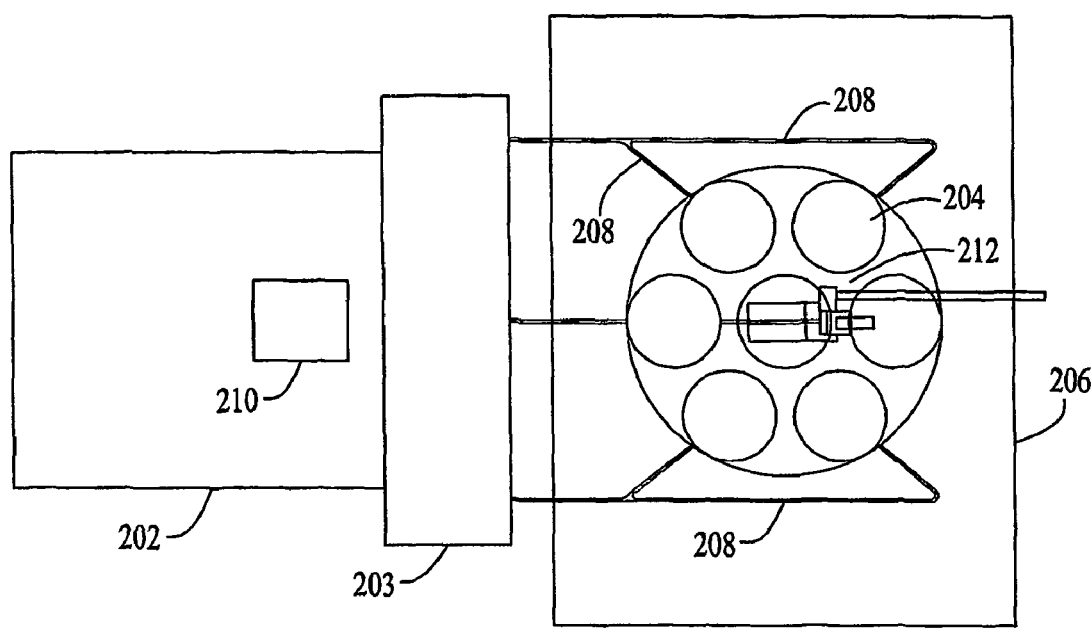
FIG. 5 shows a top view of the apparatus of FIG. 4.
Figure 8:
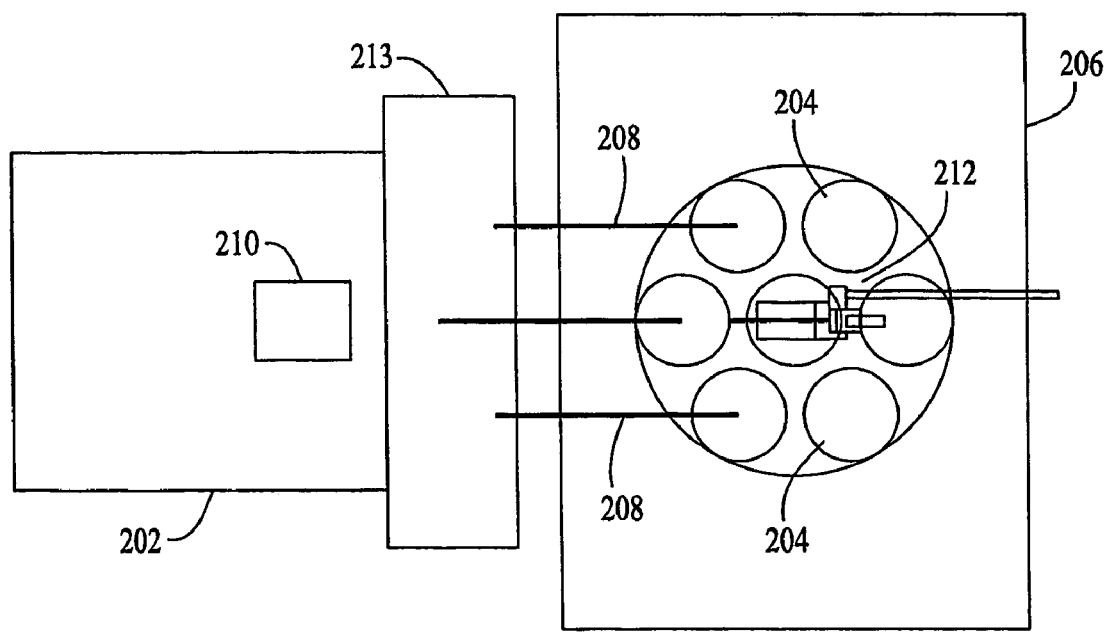
FIG. 8 shows a top view of the apparatus of FIG. 7.

Referring to FIGS. 4-6, an embodiment of another apparatus 200 for manufacturing the cleansing sponge 10 (e.g., "pourable soap") according to the present invention is shown. As shown in FIG. 4, the cleansing agent 12 in heated to about 150 to 200° F. and maintained in liquid form in a soap vessel 202. One or more sponges 11 are placed in holding caps 204 on a table 206.

As shown in the top view of the apparatus 200 in FIG. 5, molten soap 12 is transferred into each holding cap 204 via respective transfer tubes 208 from the vessel 202 by the action of a pump 210. A dosimeter 203 allows control of the amount of molten soap 12 that is transferred to each holding cap 204 via the corresponding transfer tube 208 from the vessel 202.

As shown in FIG. 6, a press 212 such as an arbor press, when lowered, compresses the sponge 10 in each holding cap 204, wherein thereafter slow release of pressure from the sponges 11 allows each sponge 11 to absorb molten soap 12 from the respective holding cap 204. Then the sponges 11 are removed from the holding caps 204 and allowed to cool/dry in a similar fashion described above, for the molten soap 12 to resolidify.

The press 212 includes press plates 213 that correspond to the holding caps 204. The press plates are attached to a support 215 that slides up and down a shaft 217 by rotary action of a lever 219 as shown by arrow 221. The lever 219 can be spring loaded to resist downward motion of the press plates 213 towards the holding caps 204.

The temperature/viscosity of the molten soap 12, the amount of compression of the sponges 11, the composition of the sponges 10, the amount of molten soap 12 in each holding cap 204 and pressure from the pump 210, are among controllable parameters that determine the characteristics of the processed sponges 10. The sponges 11 can be placed into, and removed from, the holding caps 204 manually or by an automated process.

Further, the press 212 can be operated manually or by an automated process. In one example, when a sponge is compressed in holding cap 204, the clearance between the corresponding press plate 213 and bottom of the holding cap 204 is about e.g. 1.5 inches. The table 206 can be 30 inches high and have a 40 inch by 40 inch top surface for supporting the holding caps 204 and the press 212.

Referring to the apparatus 300 in FIGS. 7-10, in a variation of the above apparatus 200, an injection/infusion process is used to inject/infuse molten soap 12 into the sponges 11 within holding caps 204. As shown in the side view and top view of the apparatus 300 in FIGS. 7 and 8 respectively, the transfer tubes 208 are connected from the vessel 202 via the dosimeter 203 to injectors 302 (e.g., hollow needles) that are installed on the support 215 of the press 212. When the press 212 is lowered (FIG. 9), the injectors 302 are inserted into sponges 11 in respective holding caps 204. Then the molten soap 12 is pumped into the sponges 11 with the injectors 302 for infusion therein.

In addition to the infusion, optionally the sponges 11 may be compressed by the press 212, as described above, wherein slow release of pressure from the sponges 11 allows each sponge 11 to further absorb molten soap 12 from the injectors 302. Then the injectors 302 are withdrawn from the sponges 11 by raising the press support 215, and the sponges 10 are removed from the holding caps 204 and allowed to cool/dry in a similar fashion described above for the molten soap 12 to solidify. The temperature/viscosity of the molten soap 12, the optional amount of compression of the sponges 11, the composition of the sponges 11, the amount and pressure of molten soap 12 from each injector 302, are among controllable parameters that determine the characteristics of the processed sponges 11.

Figure 11:
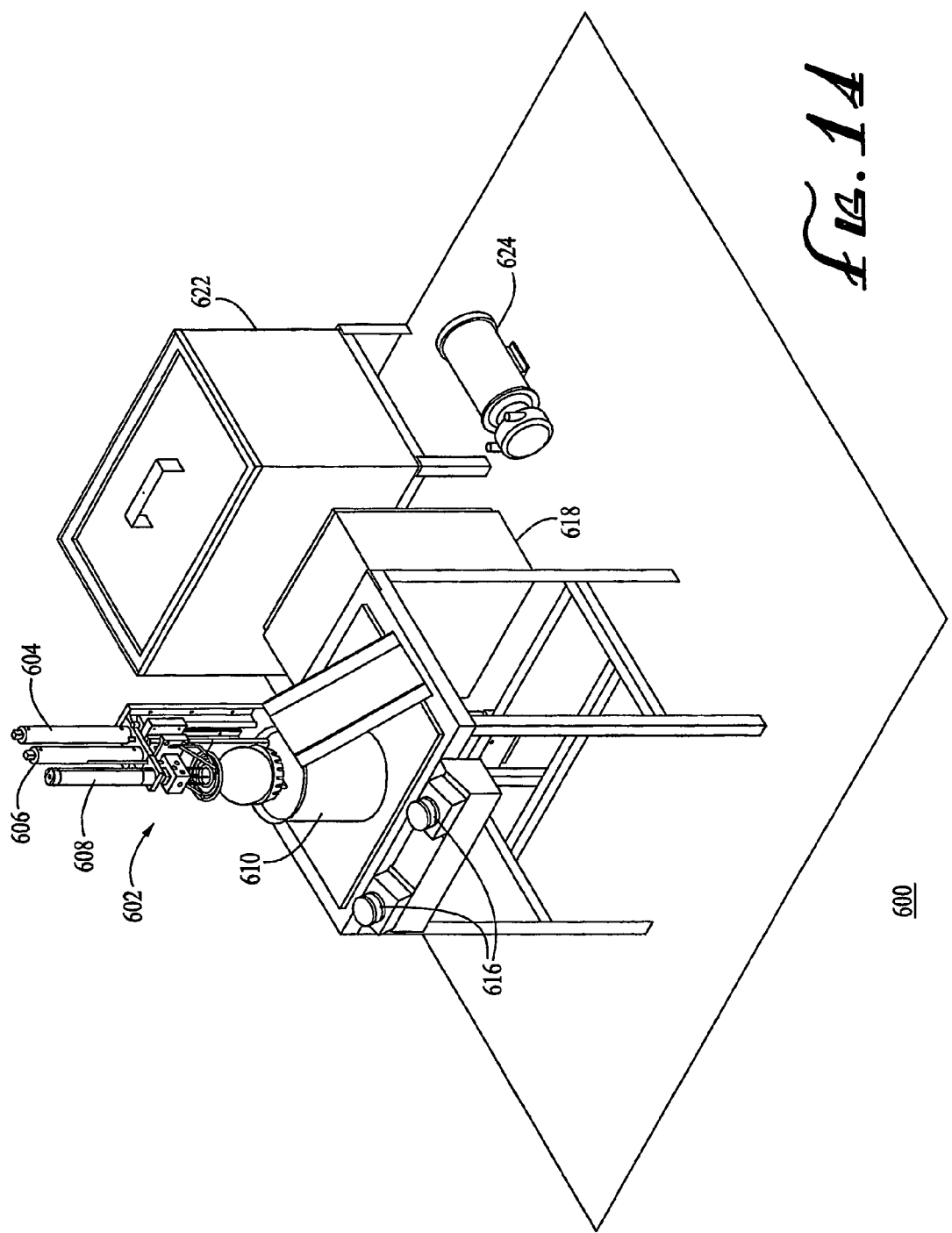
FIG. 11 shows an example of injecting a pad with cleansing agent according to the present invention.
Figure 15:
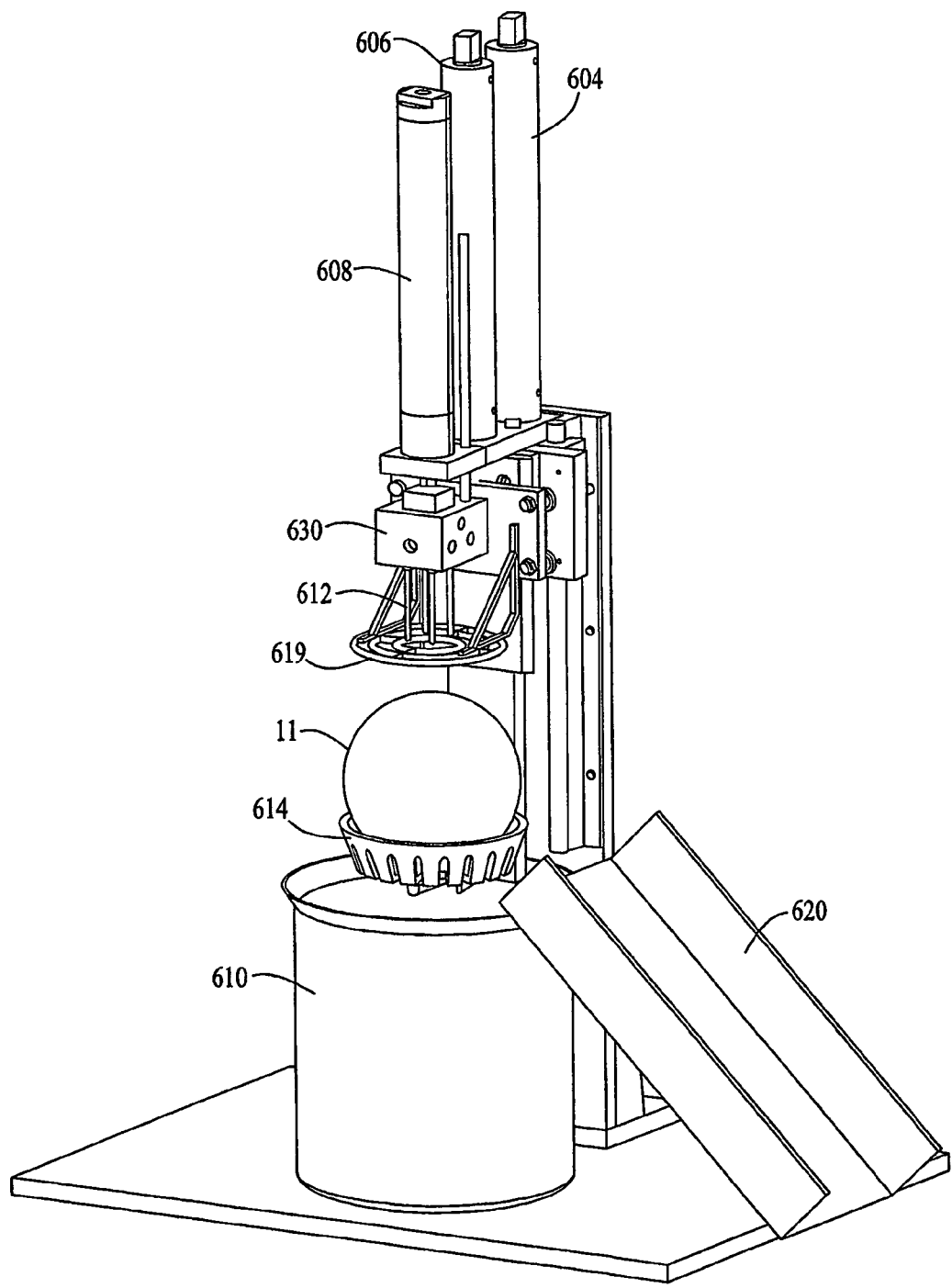
Figure 16:
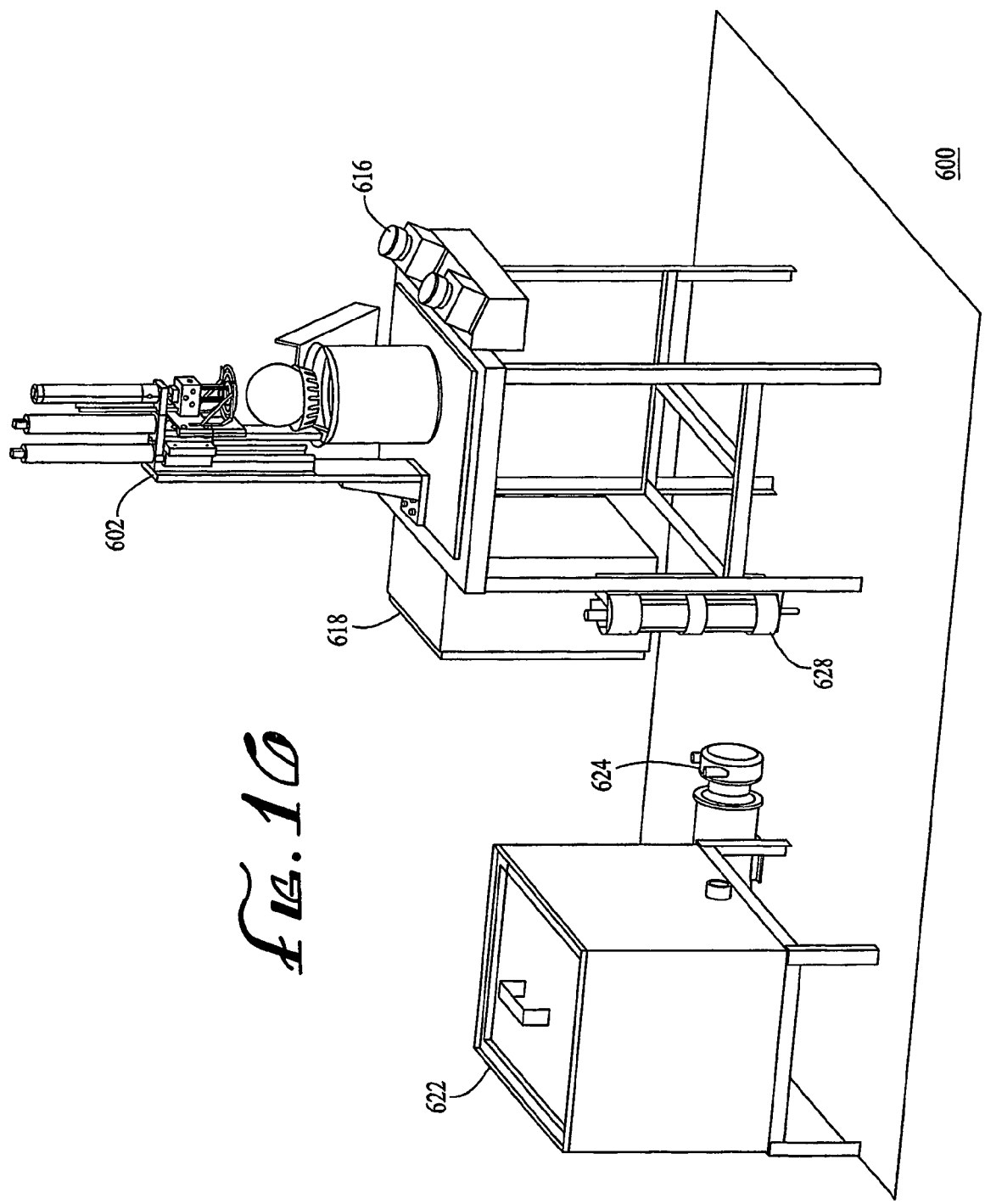
FIG. 16 shows another perspective view of the apparatus of FIG. 14.
Figure 17:
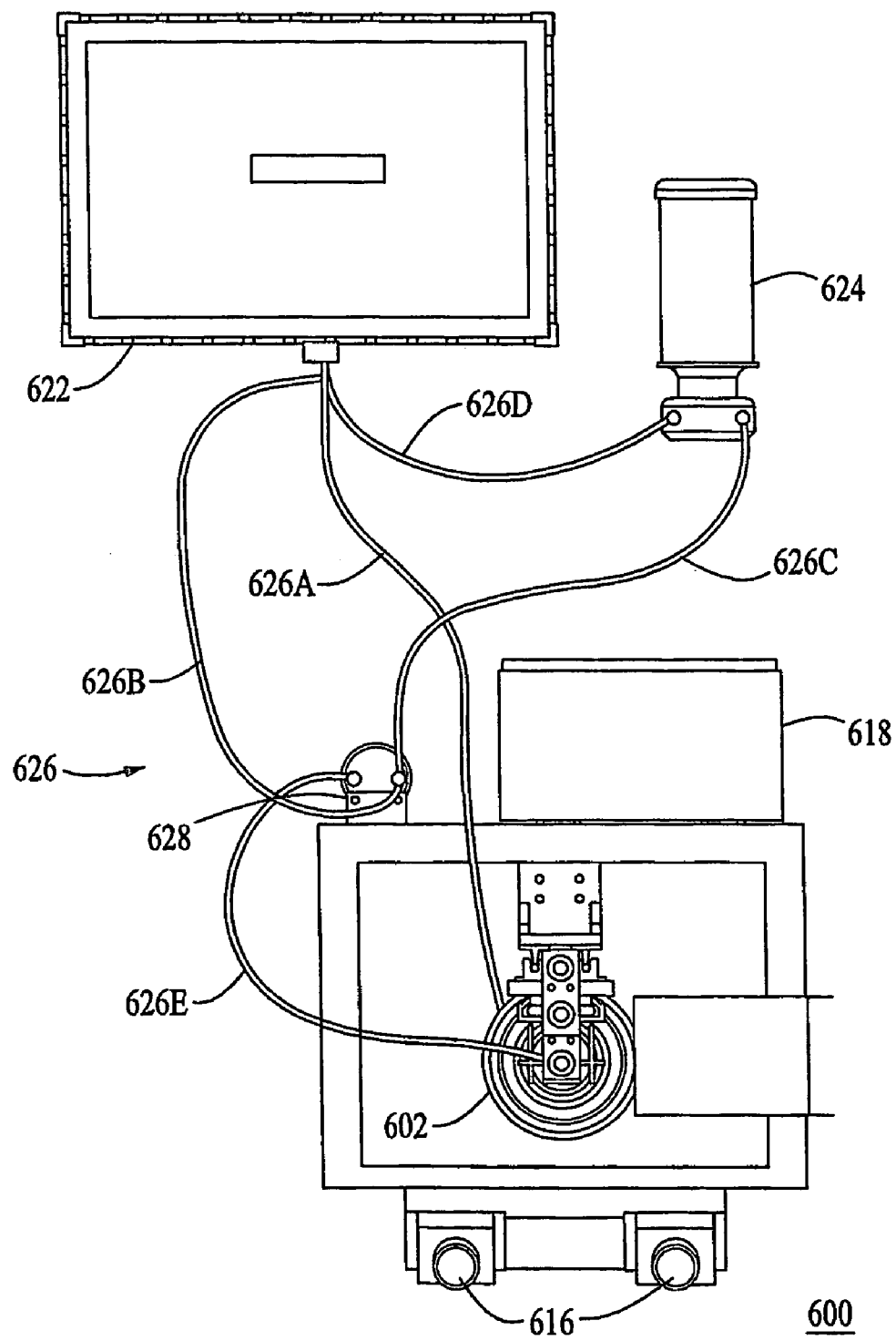
FIG. 17 shows a top view of the apparatus of FIG. 12 including tubing for flow of liquid cleansing agent therein.

As shown by example in FIG. 11, each injector 302 has several openings 304 thereon, large enough to release the molten soap 12 into each sponge 11 in a spread. FIG. 11 shows the example injector 302 partially inserted into a sponge 11 on a holding cup 204. Further, more than one injector 302 can be connected to the press 212 for insertion of multiple injectors 302 into each sponge 11, resulting in faster and/or better infusion/distribution of molten soap 12 into each sponge 11. In another version, the sponges 11 are not compressed for injection of the molten soap 12. Rather, the injectors 302 are inserted into the sponges 11, without compressing the sponges 11, to inject the molten soap 12 therein.

Preferably, the configuration of the injector (injection head) 302 and supporting devices allow selection of soap temperature, injection depth, pump output/speed, pump temperature, and delivery hose temperature. Automatic sensor activated controls for temperature is preferable. In one example, an injector 302 is about 4 inches long, about 0.07 inches in inner diameter, with about 15 openings on its sidewalls.

In another embodiment, shown in FIG. 12, instead of injectors, spraying nozzles 400 are used to spray molten soap 12 onto the exterior of the sponges 11. The amount of sprayed molten soap 12, the spray pressure and the viscosity/temperature of the molten soap 12 and the material of the sponges 11, are among parameters that can be adjusted to control amount of molten soap 12 absorbed by the sponges 11 and how far the molten soap 12 travels into the interior of the sponges 11. Further, each sponge 11 can be first compressed, and then sprayed, with decompression during or after spraying, to control the amount of molten soap absorbed by each sponge 11.

Figure 13:
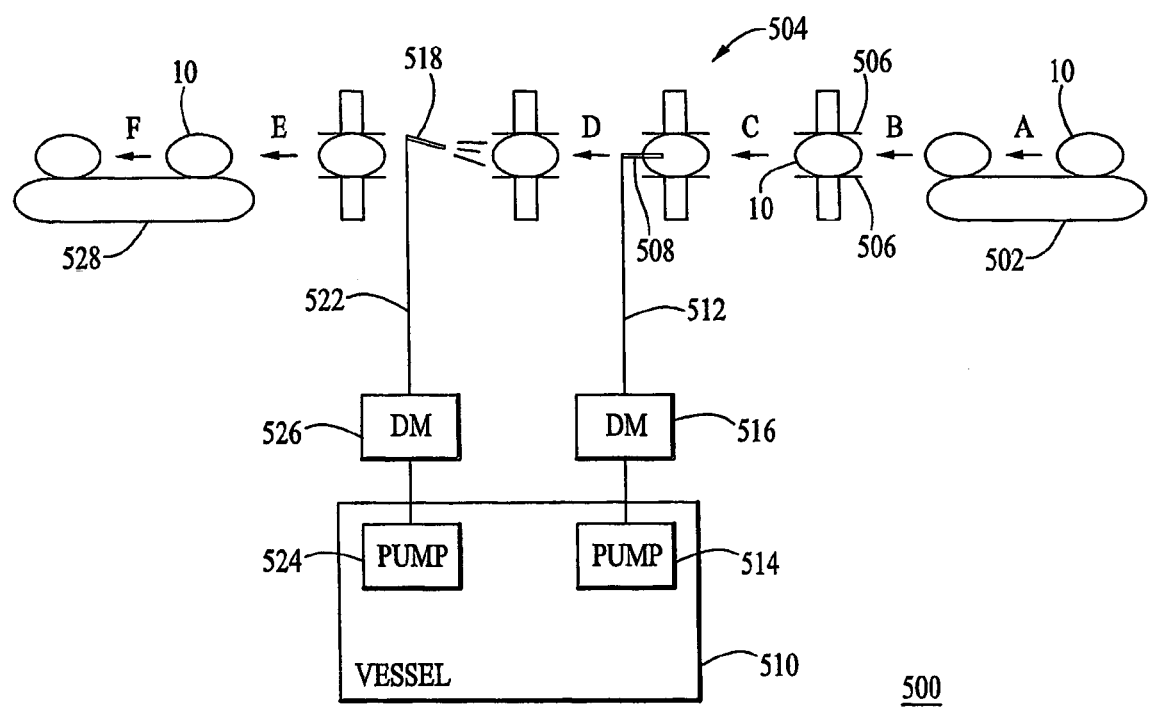
FIG. 13 shows a side view of an embodiment of another apparatus for a process of manufacturing a cleansing device pad according to the present invention.

Referring to FIG. 13, in another example infusion/impregnation apparatus 500 according to the present invention, a conveyor belt 502 leads sponges 11 into a clamping system 504 in step A. Then in step B, each sponge 11 is clamped off the belt 502 using a pair of clamps 506 (e.g., one clamp from above and one clamp from below). In step C, the clamped sponge 11 is then side injected using an injector 508 (e.g., injector 302 in FIG. 10) with preheated molten soap 12 from a vessel 510 via tubing 512 by the action of a pump 514 and dosimeter 516. As shown by example in FIG. 10, each injector 508 has large enough openings to release the molten soap 12 into each sponge 11 in a spread, wherein the molten soap 12 is maintained at a viscosity/temperature sufficient to prevent leakage out of the sponge 11 due to gravity. Further, optionally, the clamps 506 may compress the sponges 11, wherein slow release of pressure from the sponges 11 allows each sponge 10 to further absorb molten soap 12 from the injector 508. Then, each injector 508 is withdrawn from the corresponding sponge 11.

The temperature/viscosity of the soap 12, the amount of compression of the sponges 11, the composition of the sponges 11, the amount and pressure of molten soap 12 in each injector and pump pressure, are among controllable parameters that determine the characteristics of the processed sponges 11.

After a sponge 11 has been injected, optionally it is moved to a misting system where it is misted/spayed with molten soap 12 (e.g., 1 oz.) by a nozzle 518 (e.g., nozzle 400 in FIG. 12), in step D. The molten soap 12 is fed to the nozzle 518 from the vessel 510 via tubing 522 by action of a pump 524 and dosimeter 526. The misted sponge 11 is then dropped back onto another conveyer belt 528 in step E and taken off to a nearby drying rack to dry/cool in step F as described above.

In another variation, sponges 11 are loaded onto the positioning conveyer belt 502 fitted with devices (e.g., clamps 504) to accurately position each sponge 11. The sponges 11 can be unloaded off the positioning belt 502 by rotating rotisserie style impaling devices (not shown), one on the top and one on the bottom of the sponges 11. The impaling devices hold the sponges 11 as they are being side-injected by syringes (e.g., injector 508) filled with molten soap 12. The temperature of the molten soap 12 inside the syringes is controlled to keep the molten soap 12 at optimum liquidity so as to insure thorough wetting of the sponge interior. Each sponge 11 is then optionally dipped in, and/or sprayed with, molten soap 12 at a controlled temperature so as thoroughly wet the exterior of the sponge 11 to a depth sufficient to meet the previously injected soap core. The sponges 11 are then spun to remove any excess soap from their surface. Then the sponges 11 are unloaded from the impaling holders into a drying system.

Preferably, the soap injection depth in each sponge 11 is half the diameter of the sponge 11. This is the depth to which the injection device (e.g., nozzle) is inserted into the sponge 11. The injection depth is preferably a central location within the sponge 11 and is controllable to accommodate varying sponge sizes, including allowing injection of soaps of various density as injection point moves from center towards the surface of the sponge 11. Further, different sides of the sponge 11 can be treated (e.g., injected, sprayed, etc.) differently. As such, soap is selectively applied to control exfoliation properties wherein different soap formulations are selectively applied to different parts of the sponge. For example, this may provide greater cleansing versus greater moisturizing on one side of sponge combination than another side.

The injection time (dwell cycle), can be variable depending on the composition of soap 12 used. This is the time that the injection device will remain in position within the sponge 11 while it injects the molten soap 12 into the sponge 11. The cycle time may be affected by the sponge material and density variations. The injection device can be fitted with a positioning holder for the sponges 11 as well as a "stripper" device to strip the sponge as the injection device is withdrawn. Preferably, the injector head temperature is maintained at about e.g. 120 to 200° F., to assure that the molten soap 12 flows through it freely. Further, the injector supply hose temperature is preferably maintained at about e.g. 120 to 200° F., to allow flow of molten soap 12 from the pump. Further, the injection pump temperature is preferably maintained at about e.g. 120-200° F.

The injection supply vessel/kettle temperature is preferably maintained at about e.g. 120-200° F. Generally, it is preferable for such temperature ranges to be as low as possible consistent with the injection process. This can be achieved using a small electric kettle of sufficient size to support production use rates, and may contain a light agitation system to prevent "wall scalding" of the soap 12. The supply kettle, the supply pump, the supply pipe and the injector are preferably equipped with temperature sensors having automatic control to maintain the desired temperature. A fire control system may also be included.

As such, according to example alternative embodiments of the present invention, in an Immersion-Compression-Absorption process, each sponge 11 is immersed in molten soap 12 and compressed to force air in the sponge to be evacuated from the sponge 11 and induce the transfusion of the molten soap 12 into the sponge 11 to fill the cell structure (pores) vacated by the evacuated air.

Alternatively, in an Immersion-Compression-Injection process, each sponge 11 is immersed in molten soap 12 and compressed to force air in the sponge to be evacuated from the sponge 11 and induce the transfusion of the molten soap 12 into the sponge to fill the cell structure vacated by the evacuated air. The transfusion action is enhanced by the use of an injection device to transfuse additional molten soap 12 into the core of the sponge 11.

Alternatively, in an Immersion-Multiple Compression-Absorption process, each sponge 11 is immersed in molten soap 12 and compressed multiple times to force air in the sponge to be evacuated from the sponge 11 and induce the transfusion of the molten soap 12 into the sponge 11 to fill the cell structure vacated by the evacuated air.

Alternatively, in an Immersion-Multiple Compression-Injection process, each sponge 11 is immersed in molten soap 12 and compressed multiple times to force air in the sponge 11 to be evacuated from the sponge 11 and induce the transfusion of the molten soap 12 into the sponge 11 to fill the cell structure vacated by the evacuated air. The transfusion action is enhanced by the use of an injection device to transfuse additional molten soap 12 into the core of the sponge 11.

In yet another alternative, using an Immersion-Vacuum process, each sponge 11 is immersed in molten soap 12 located in a vacuum chamber which evacuates air from the sponge substrate and induces the transfusion of the molten soap 12 into the sponge 11 to fill the cell structure vacated by the evacuated air.

The above examples alternative processes are provided for better understanding of embodiments of the present invention, and as those skilled in the art will recognize, the present invention is not limited to these examples. Further, other equipment for molten soap transfusion/injection for manufacturing the sponges 10 according to embodiments of the present invention may be utilized.

An example is a Converging Conveyor Metal Mesh Conveyor Belt (not shown), comprising two opposed motorized metal conveyor belts to provide a constantly moving controlled compression and release of compression on sponge substrates fed into it from a feed hopper. The substrates are then immersed in a heated molten soap bath so as to evacuate the air from the sponge substrates and induce the transfusion of the molten soap 12 into the sponges 11 to fill the cell structure vacated by the evacuated air. The transfused sponges 11 are released at the opposite end of the process.

Another example is a Multiple Interlocking Finger Compression Baskets Conveyor (not shown), comprising two opposed motorized metal conveyor belts on which multiple opposing halves of interlacing metal mesh compression baskets are mounted. The baskets pick up hopper fed sponge substrates and provide a constantly moving controlled compression and release of compression on the sponge substrates, immersed in a heated molten soap bath, so as to evacuate the air from the sponge substrate and induce the transfusion of the molten soap 12 into the sponges 11 to fill the cell structure vacated by the evacuated air. The transfused sponges are released at the opposite end of the process.

Yet another example is a Multiple Interlocking Finger Compression Basket Ferris Wheel Conveyor (e.g., FIG. 21), comprising a vertically mounted wheel on which multiple opposing halves of interlacing metal mesh compression baskets are mounted. The baskets pick up hopper fed sponge substrates and provide a constantly moving controlled compression and release of compression on the sponge substrates, immersed in a heated molten soap bath, so as to evacuate the air from the sponge substrate and induce the transfusion of the molten soap 12 into the sponge to fill the cell structure vacated by the evacuated air. The transfused sponges 11 are released at the opposite ends of the process. Yet another example shown in FIGS. 14-17 comprises a sponge soap application/injection system including a semi-automatic machine 600, capable of processing at least one sponge 11 automatically by either dipping the sponge 11 in a preheated soap solution 12 or by injection the soap solution 12 internally into the sponge 11, or a combination of both operations. The machine 600 allows complete operator control over all process variables involved with the soap applying operation. The machine 600 comprises a pneumatically operated press system 602 where three independently controlled slides 604, 606, 608, perform the different process tasks. The first slide 604 elevates the sponge 11 into a vat 610 filled with preheated soap solution 12. The second slide 606 provides a compression operation to the sponge 11. The third slide 608 inserts applicator needles 612 into the sponge and then injects a specific volume of soap 12 into the sponge 11.

The process includes loading a sponge 11 into a holding fixture 614 wherein automatic operation is then initiated by pressing a two-handed safety push button system 616 to start the machine operation. A PLC (programmable logic control) 618 controls all the sequencing and operation of the machine functions. The sequence and timing are fully programmable via an operator keypad and display screen (not shown). Although the process can be varied, the basic operation includes the steps of compressing the sponge 11 in the pneumatic press by the slide 608 lowering a compression plate 619 unto the sponge 11 to a predefined height, lowering the sponge 11 into the liquid/molten bath 610 of heated soap solution 12 and then injecting molten soap 12 into the sponge 11 via several hypodermic style needles 612. The control 618 will then remove the needles 612, uncompress the sponge 11 and lift it from the application vat 610 allowing the soap solution 12 to coat and fill the sponge 11 as desired. The sponge 11 is then be ejected into a delivery chute 620 where it can be transferred onto drying racks. All timing functions will also be controlled via the PLC 618 and can be modified by the operator keypad and terminal.

The system 600 further includes a soap melting vat 622, a circulation pump 624 and heated hoses 626 to maintain the temperature of the soap solution throughout the system. The heated hoses 626 include: a Heated Drain Line 626A, a Heated Return Line 626B, a Heated Supply Line 626C, a Heated Suction Line 626D and a Heated Pressure Line 626E. The Pressure Line 626E provides soap 12 from a heated metering pump 628 to a needle injection block 630 which is also temperature controlled: The Heated Return Line 626B returns unused soap 12 back to the main melting vat 616 for reuse.

Figure 18:
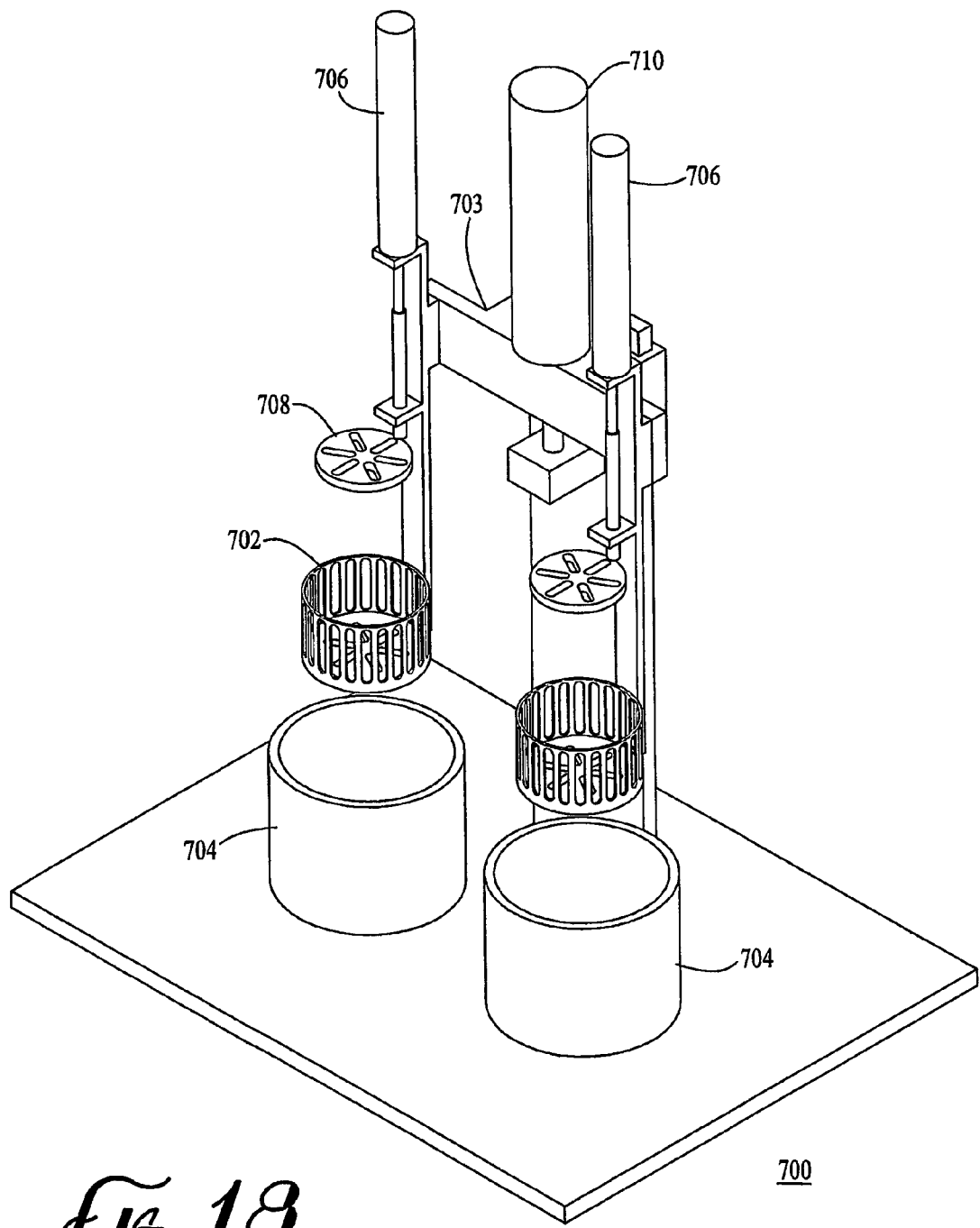
FIG. 18 shows an example perspective view of an embodiment of another apparatus for a process of manufacturing a cleansing device pad according to the present invention.

Yet another example shown in FIG. 18 comprises an Air Cylinder Press including a pneumatically driven press system 700 used to compress two sponges in holding baskets 702 that are lowered into soap solution filled cups 704. A slide assembly 730 includes two slides 706 and a third slide 710. The two slides 706 (e.g., air cylinder lifts) lower compression plates 708 onto the sponge in the holding baskets 702 to compress the sponges. The compressed sponges 11 are then lowered by a third slide 710 into the cups 704 of molten soap 12. The compression plates 708 are lifted, allowing the sponges to absorb molten soap 12. After absorption of liquid soap 12 into the sponges, the slide 710 lifts the sponges out of the cups 704, sponges are removed from the baskets 702 and allowed to cool down. The system 700 can be automated by adding an automatic loader and conveyor system, and controlled with a PLC.

Figure 19:
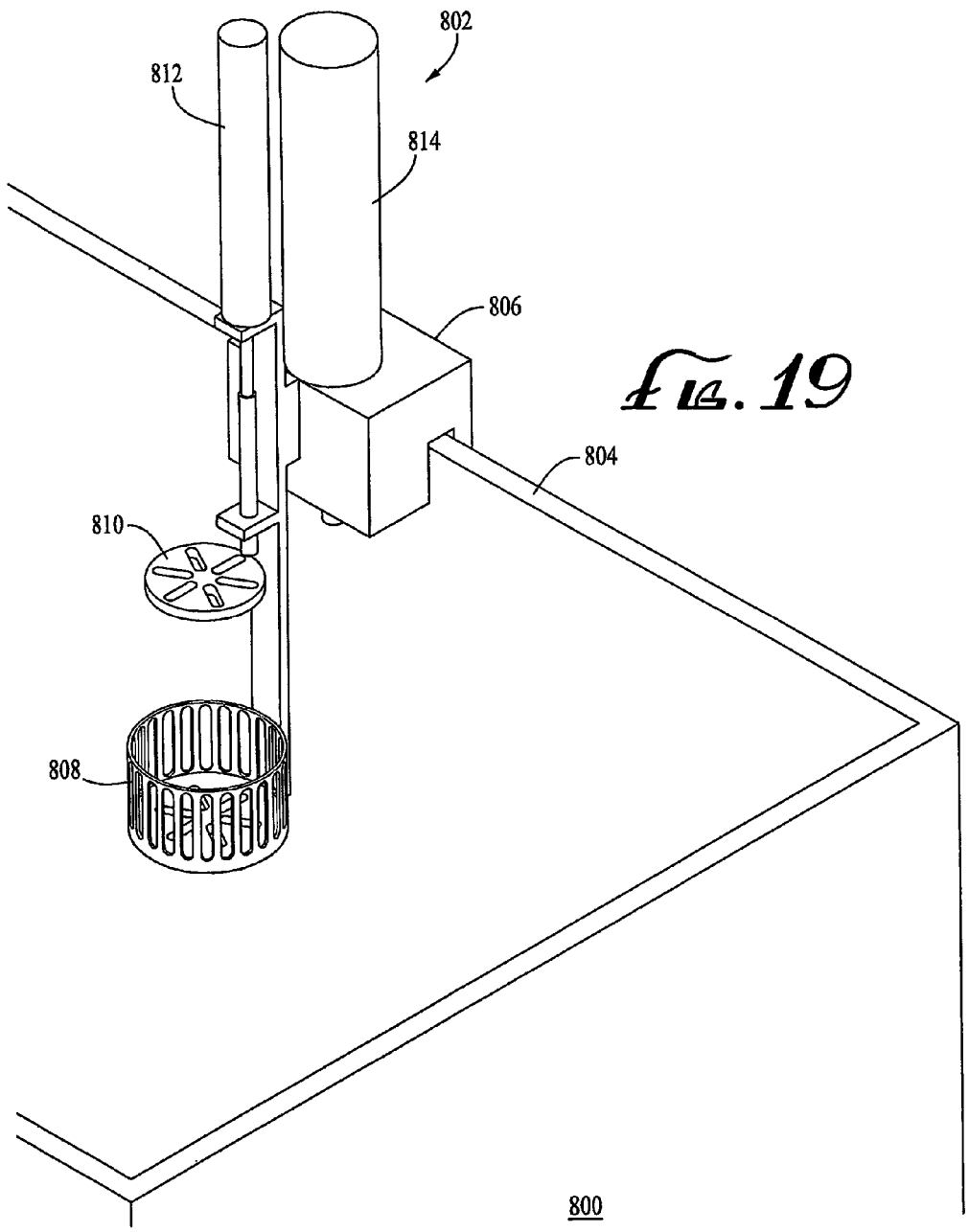
FIG. 19 shows an example perspective view of an embodiment of another apparatus for a process of manufacturing a cleansing device pad according to the present invention.

Yet in another example shown in FIG. 19, a system 800 includes a pneumatically driven slide assembly 802 that is attached to the side of a melting vat 804 by a clamp 806. A sponge is loaded into a basket 808 where it is automatically compressed via a compression plate 810 operated by a slide 812, and lowered into the molten soap solution 12 in the vat 804 by a second slide 814. The compression plate 810 is then lifted, allowing the sponge to absorb molten soap 12. After absorption of liquid soap 12 into the sponge, the slide 812 lifts the sponge out of the vat 804, the sponge is removed from the basket 808 and allowed to cool down. Multiple systems 800 could be used to increase production rates, and the systems 800 can be controlled with a PLC.

Figure 20:
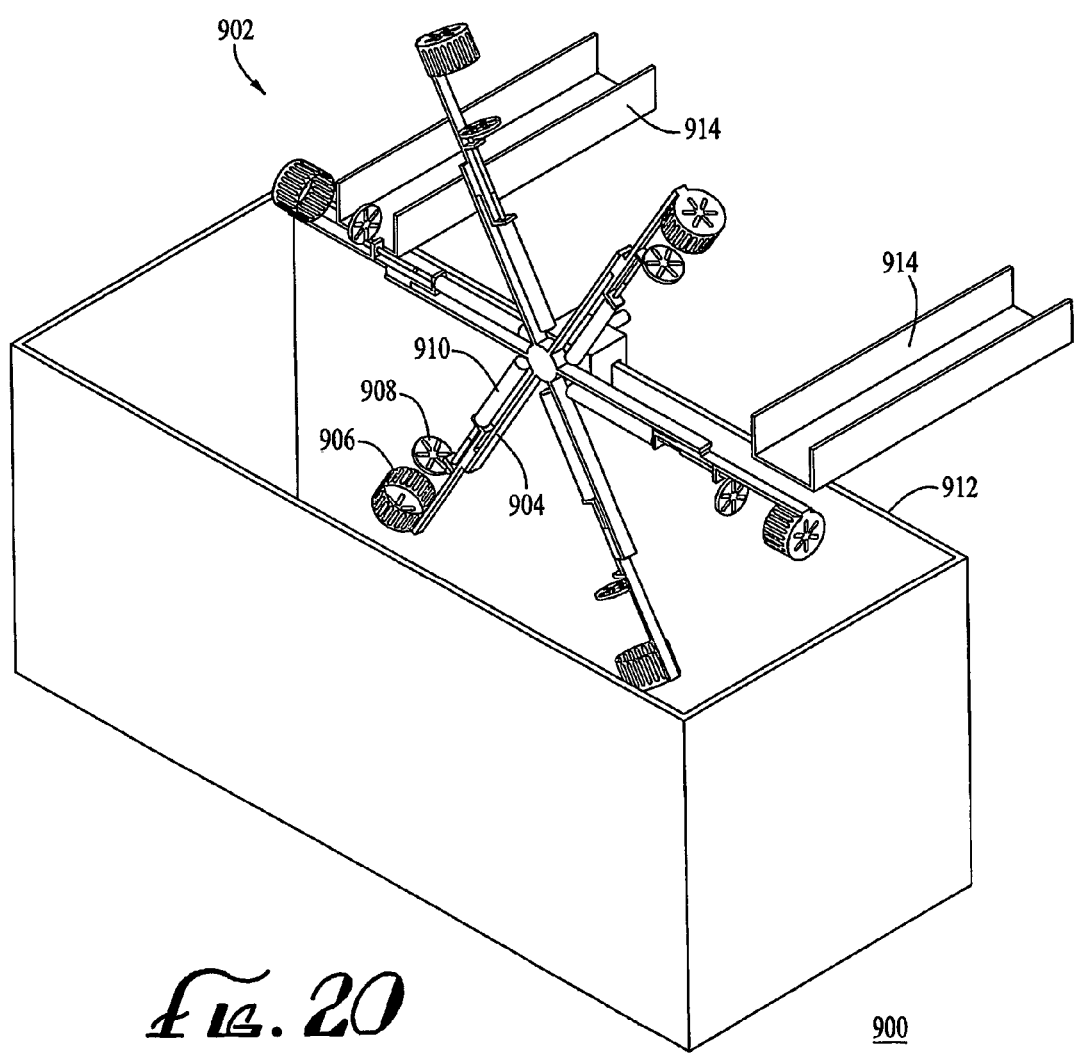
FIG. 20 shows an example perspective view of an embodiment of another apparatus for a process of manufacturing a cleansing device pad according to the present invention.

Yet another example shown in FIG. 20 comprises a Carousel System 900 including a multiple arm carousel 902 used to compress and fill the sponges in a rotary operation. Each carousel arm 904 includes a basket 906 to hold a sponge, compression plate 908 to compress the sponge and slide 910 to operate the compression plate 908 to compress the sponge. The carousel 902 is rotated whereby the carousel arms 904 dip the baskets 906 in molten soap 12 in the vat 912. Before each basket is dipped in the vat 912, the compression plate 908 compresses the sponge in the basket 906 and when the basket 906 is dipped into the molten soap 12, the compression plate 908 is lifted to allow the sponge to absorb soap while dipped in the vat 912. Thereafter, the dipped sponge 12 is removed from the basket 906 via chutes 914 and allowed to cool. Conveyors or loaders can be incorporated into the system 900 to automatically load the carousel arms 904 for high-speed production.

Figure 21:
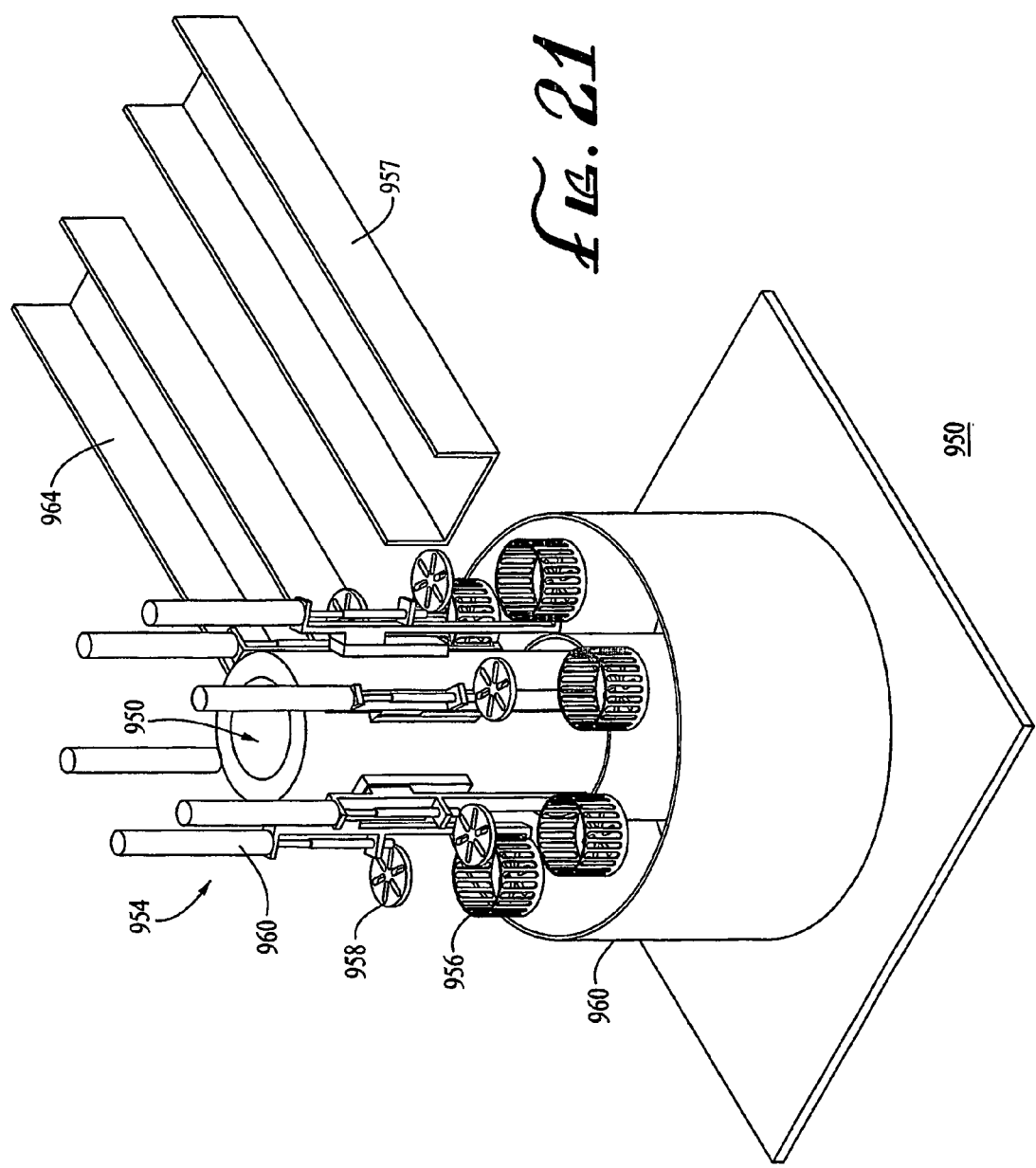
FIG. 21 shows an example perspective view of an embodiment of another apparatus for a process of manufacturing a cleansing device pad according to the present invention.

Further, in the example shown in FIG. 21, a Rotary System 950 that is an automated, stand-alone system includes a rotating drum 952 used to apply molten soap to the sponges in a continuous rotary process. The drum 952 includes arms 954, wherein each arm 954 includes a basket 956 to hold a sponge, compression plate 958 to compress the sponge and slide 960 to operate the compression plate 958 to compress the sponge. Sponges are placed into the baskets 956 via a chute 957. The drum 952 is lowered whereby the arms 954 dip the baskets 956 in molten soap 12 in the vat 962. Before each basket 956 is dipped in the vat 962, the compression plate 958 compresses the sponge in the basket 956 and when the basket 956 is dipped into the molten soap 12, the compression plate 958 is lifted to allow the sponge to absorb soap while dipped in the vat 962. The drum 952 is then lifted to raise the baskets 956 from the molten soap 12 in the vat 962, and the dipped sponges 12 are removed from the basket 956 via the chute 964 and allowed to cool. The process is repeated for a next set of sponges.

The above example equipments are provided for better understanding of embodiments of the present invention, and as those skilled in the art will recognize, the present invention is not limited to these examples.

Weight control for the final product (i.e., the cleaning sponge 10 resulting from the above processes) can be performed e.g. manually on a trial and error basis by squeezing and a weight balance. The final weight after any "adjustment" is determined by shelf life testing which should yield information on weight loss due to moisture transfer or lack thereof. Preferably, an automated weight control process is utilized by controlling the sponge immersion and injection times and temperatures. Further, a controlled squeezing device may be utilized which presses the cleansing sponges 10 one at a time between two moving belts to gain the desired weight. In one example, final product weight adjustments can be made by injecting additional molten soap 12 into the cleansing sponge 10 using a heated syringe to reach a level of e.g. about 7+/−0.2 ounces of soap in the cleansing sponge 10.

In use, the cleansing sponge 10 is applied for cleaning an object in conjunction with a solvent such as hard or soft water. The solvent dissolves the solidified soap 12 into a solution that includes quantities of the solvent and dissolved cleansing agent for cleansing the object. The cleansing sponge 10 can be used in this manner multiple times without the need for application of other cleansing agent to the pad. As such, the cleansing sponge 10 is a self-contained, long lasting product that does not require the user to reapply cleansing agents to the pad with every use.

The above processes and apparatuses accommodate various pads 11 and various cleansing agents 12 such as the pourable soap formulations according to embodiments of the present invention. One embodiment of the present invention is based on the use of pourable soaps in pads, which yielded several unexpected results, such as long lasting, effectiveness of lather profile in hard water and a simpler process for incorporating a pourable soap into pads.

The cleansing agent 12 can include one or more cleansing substances/formulations that can be applied to the pad 11 in various amounts, and is therefore not limited to one cleansing substance. For example, the multiple soap formulations can include: (1) soaps-only formulations, (2) soap and synthetic detergent combinations, (3) sodium TEA soap combinations superfatted with excess fatty acid (4) all of the above in addition to special additives, such as antimicrobials, etc. One or more example formulations from each group can be applied to a pad 11 in one or more dippings using the manufacturing equipment described above. As such, a multiple dipping and/or injection process is used in which different soap formulations are applied to the same pad to produce a multiple effect cleansing pad. This process can further be useful in combining ingredients which cannot be mixed together in the same soap formula but can be brought together when different soap formulas are activated together on the cleansing pad with water.

Other examples for multiple dipping processing include: (1) applying a different color to the pad in each dipping process, (2) applying two different soap formulations to the pad in each dipping process, one soap formulation including active "A" (e.g., an antimicrobial agent) and another soap formulation including active "B" (e.g., a moisturizer), and (3) applying a soap to the pad in one dipping process, and in another process applying an ingredient that is incompatible with soap and with anionic detergents, incorporating that ingredient in a wax-like base that melts in the temperature range of about 120-140° F. An example for an incompatible ingredient can be a cationic surfactant, such as cocyl trimethyl ammonium chloride or dipalmityl dimethyl ammonium sulfate, which would provide conditioning and skin-feel properties.

Many alterations and modifications may be made by those skilled in the art without departing from the spirit and scope of the invention. Therefore, it must be understood that the illustrated embodiment has been set forth only for purposes of example and that it should not be taken as limiting the invention as defined by the following claims. For example, though in the example in the above description the pad is impregnated with a cleansing agent, other agents instead of, or in addition to, can be used to impregnate the pad.

The words used in this specification to describe the invention and its various embodiments are to be understood not only in the sense of their commonly defined meanings, but to include by special definition in this specification structure, material or acts beyond the defined meanings. Thus if an element can be understood in the context of this specification as including more than one meaning, then its use in a claim must be understood as being generic to all possible meanings supported by the specification and by the words itself.

The definitions of the words or elements of the following claims are therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below, or that a single element may be substituted for two or more elements in a claim.

Insubstantial changes from the claimed subject matter as viewed by a person with ordinary skill in the art, now known or later devised, are expressly contemplated as being equivalent within the scope of the claims. Therefore, obvious substitutions now or later known to one with ordinary skill in the art are defined to be within the scope of the defined elements.

The claims are thus to be understood to include what is specifically illustrated and described above, what is conceptually equivalent, what can be obviously substituted and also what essentially incorporates the essential idea of the invention.

What is claimed is:

1. A personal cleansing device comprising: (a) a web of fibers forming a substrate and (b), a pourable sodium soap having a melting point of 120° F. to 160° F. impregnated substantially throughout the interior of the substrate, and occupying interstitial spaces between the fibers in a quantity sufficient for multiple uses of the substrate in conjunction with a solvent that dissolves the pourable sodium soap for personal cleansing purposes, wherein the pourable sodium soap comprises:
    at least two sodium soaps generated from (i), fatty acids of oils selected from the group consisting of palm oil, palm kernel oil, coconut oil, olive oil, castor oil, safflower oil, and (ii), fatty acids of tallow, and
    5% to 35% glycerine and up to 10% propylene glycol, and further wherein the personal cleansing device produces lather in both hard as well as soft water.

2. The personal cleansing device of claim 1 wherein the pourable sodium soap comprises between 1 and 20% sodium oleate.

3. The personal cleansing device of claim 1 wherein the oils are organically produced oils.

4. The personal cleansing device of claim 1, wherein the pourable sodium soap comprises one or more of sugars, polyhydroxy compounds other than glycerine and amino alcohols.

5. The personal cleansing device of claim 1 wherein the pourable sodium soap contains about: 20 to 30% of an amino alcohol, 7 to 19% Cocoate sodium soap, 14 to 36% Palmitate sodium soap, 7 to 9% Glycerine and 5 to 22% Stearic acid.

6. The personal cleansing device of claim 1 wherein the pourable sodium soap contains about: 10% stearic acid, a fat charge in the range of 41.5 to 44.0%, and a palm oil to coconut oil ratio of 80 to 20.

7. The personal cleansing device of claim 1 wherein the pourable sodium soap contains about: 5 to 12% stearic acid; 35 to 50% fat charge and Palm oil to Coconut oil ratios from 50:50 to 90:10.

8. The personal cleansing device of claim 1 wherein the pourable sodium soap contains about 2 to 35% triethanolamine.

9. The personal cleansing device of claim 1 wherein the pourable sodium soap includes about: 20 to 30% Triethanolamine, 7 to 19% Cocoate sodium soap, 14 to 36% Palmitate sodium soap, 7 to 9% Glycerine and about 5 to 22% Stearic acid.

10. The personal cleansing device of claim 1 wherein the pourable sodium soap includes about: 10% stearic acid, a fat charge in the range of 41.5 to 44.0%, and a palm oil to coconut oil ratio of 80 to 20.

11. The personal cleansing device of claim 1 wherein the pourable sodium soap includes about: 5 to 12% stearic acid; 35 to 50% fat charge and Palm oil to Coconut oil ratios from 50:50 to 90:10.

12. The personal cleansing device of claim 1 wherein the pourable sodium soap includes, by weight percentage about:
Glycerine from 10 to 30%,
Sodium Cocoate from 8 to 20%,
Sodium Palmitate from 12 to 20%,
Sodium Ricinoleate from 9 to 17%,
Safflower Oil Soap from 2 to 5%,
Sorbitol from 0 to 8%,
Sorbitan Oleate from 2 to 8%,
Soybean Protein from 2 to 8%,
and Titanium Dioxide from 0 to 0.2%.

13. The personal cleansing device of claim 1 wherein the substrate comprises synthetic materials.

14. The personal cleansing device of claim 1 wherein the substrate comprises naturally occurring materials.

15. The personal cleansing device of claim 1 wherein the substrate is reticulated.

16. The personal cleansing device of claim 1 wherein the substrate is non-reticulated.

17. The personal cleansing device of claim 1 wherein the substrate is selected from the group consisting of porous polyurethane, polyethylene or cellulose.

18. The personal cleansing device of claim 1 wherein the substrate comprises a sponge.

19. The personal cleansing device of claim 1 wherein the substrate comprises woven materials.

20. The personal cleansing device of claim 1 wherein the substrate comprises non-woven materials.

21. The personal cleansing device of claim 1 wherein the substrate comprises cotton and loofah-based materials.

22. The personal cleansing device of claim 1 wherein the weight ratio of pourable sodium soap to substrate is between about 2 to 1 and 10 to 1.

23. The personal cleansing device of claim 1 wherein the weight ratio of pourable sodium soap to substrate is about 7 to 1.

24. The personal cleansing device of claim 1 further including fragrances.

25. The personal cleansing device of claim 1 further including skin moisturizers.

26. The personal cleansing device of claim 1 further including one or more of anti-cellulite substances, anti-aging substances, herbal substances, natural extracts and synthetic extracts.

27. The personal cleansing device of claim 1 further including colorants.

28. The personal cleansing device of claim 1 further including one or more active ingredients comprising sunscreen agents, antimicrobials, antiseptics and/or healing agents and combinations thereof.

29. The personal cleansing device of claim 1 further including one or more skin feel additives.

30. The personal cleansing device of claim 1 wherein the pourable sodium soap is generated by (i) heating the oil or tallow fatty acid, (ii) reacting the oil or tallow fatty acid with sodium hydroxide, and (iii) adding at least one additive selected from the group consisting of group consisting of sugars, polyhydroxy compounds and amino alcohols.

31. The personal cleansing device of claim 30 wherein the at least one additive is a polyhydroxy compound other than glycerine at up to 10%, based on the total weight of the pourable sodium soap.

32. The personal cleansing device of claim 30 wherein the at least one additive is a sorbitol at a concentration of up to 10%, based on the total weight of the pourable sodium soap.

33. The personal cleansing device of claim 30 wherein the at least one additive is an amino alcohol present at a concentration of 5% to 30%, based on the total weight of the solid cleansing agent.

34. The personal cleansing device of claim 33 wherein the amino alcohol is triethanolamine.

35. The personal cleansing device of claim 1 wherein the pourable sodium soap is generated from fatty acids of oils selected from the group consisting of palm oil, palm kernel oil, coconut oil, olive oil, castor oil, and safflower oil and fatty acids of tallow and the pourable soap is formed by the sequential steps of (i) hydrolyzing the oil or tallow with high-pressure steam to yield crude fatty acids and glycerine, (ii) removing the glycerine, (iii) purifying the crude fatty acids by distillation, (iv) neutralizing the fatty acids with a strong alkali to produce soap and water, and (v) adding to neutralized mixture of step (iv) glycerine and at least one additive selected from the group consisting of group consisting of sugars, polyhydroxy compounds and amino alcohols.

36. The personal cleansing device of claim 1 wherein the pourable sodium soap is essentially free of synthetic detergents.

37. The personal cleansing device of claim 36 wherein the pourable sodium soap agent is free of synthetic detergents.

38. The personal cleansing personal device of claim 1 that produces foam in hard water having greater than about 150 ppm of calcium and magnesium metal cations.

39. The personal cleansing device of claim 38 that produces foam in hard water having greater than about 300 ppm of calcium and magnesium metal cations.

* * * * *